United States Patent [19]

Christensen et al.

[11] 4,335,043
[45] Jun. 15, 1982

[54] SUBSTITUTED N-METHYLENE DERIVATIVES OF THIENAMYCIN

[75] Inventors: Burton G. Christensen, Metuchen; William J. Leanza, Berkeley Heights; Kenneth J. Wildonger, Somerville, all of N.J.

[73] Assignee: Merck & Co., Inc., Rahway, N.J.

[21] Appl. No.: 84,013

[22] Filed: Oct. 11, 1979

Related U.S. Application Data

[60] Division of Ser. No. 852,425, Nov. 17, 1977, Pat. No. 4,194,047, which is a continuation-in-part of Ser. No. 733,654, Oct. 18, 1976, abandoned, which is a continuation-in-part of Ser. No. 676,261, Apr. 12, 1976, abandoned, which is a continuation-in-part of Ser. No. 634,296, Nov. 21, 1975, abandoned.

[51] Int. Cl.$^3$ .................... C07D 487/04; A61K 31/40
[52] U.S. Cl. .............................................. 260/245.2 T
[58] Field of Search .................. 260/245.2 T; 546/272

[56] References Cited

U.S. PATENT DOCUMENTS

4,172,144 10/1979 Bouffard et al. ............. 260/245.2 T
4,232,030 11/1980 Christensen .................. 260/245.2 T

FOREIGN PATENT DOCUMENTS

848545 5/1977 Belgium .

Primary Examiner—Mark L. Berch
Attorney, Agent, or Firm—Donald J. Perrella; Hesna J. Pfeiffer

[57] ABSTRACT

Disclosed are substituted N-methylene derivatives of thienamycin which may be represented by the following structural formula:

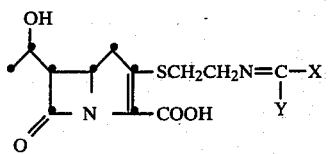

wherein X and Y are selected from the group consisting of hydrogen, R, OR, SR, and NR$^1$R$^2$ wherein, inter alia, R is substituted or unsubstituted: alkyl, alkenyl, alkynyl, cycloalkyl, cycloalkylalkyl, aryl, aralkyl, heteroaryl, heteroaralkyl, heterocyclyl, and heterocyclylalkyl; R$^1$ and R$^2$ are hydrogen or R. Such compounds and their pharmaceutically acceptable salt, ether, ester and amide derivatives are useful as antibiotics. Also disclosed are processes for the preparation of such compounds; pharmaceutical compositions comprising such compounds; and methods of treatment comprising administering such compounds and compositions when an antibiotic effect is indicated.

3 Claims, No Drawings

SUBSTITUTED N-METHYLENE DERIVATIVES OF THIENAMYCIN

This is a division of application Ser. No. 852,425, filed Nov. 17, 1977 now U.S. Pat. No. 4,194,047 which in turn is a continuation-in-part of Ser. No. 733,654, filed Oct. 18, 1976, now abandoned; which is a continuation-in-part of Ser. No. 676,261, filed Apr. 12, 1976, now abandoned; which in turn is a continuation-in-part of Ser. No. 634,296, filed Nov. 21, 1975, now abandoned.

BACKGROUND OF THE INVENTION

This invention relates to certain substituted N-methylene derivatives of the new antibiotic thienamycin. Such compounds and their pharmaceutically acceptable salt, ether, ester, and amide derivatives are useful as antibiotics. This invention also relates to processes for the preparation of such compounds; pharmaceutical compositions comprising such compounds; and methods of treatment comprising administering such compounds and compositions when an antibiotic effect is indicated.

Thienamycin is disclosed and claimed in co-pending, commonly assigned U.S. Patent Application Ser. No. 526,992, filed Nov. 25, 1974 (now U.S. Pat. No. 3,950,357 issued Apr. 13, 1976), which is incorporated herein by reference since thienamycin may be employed as a starting material in the preparation of the compounds of the present invention.

Thienamycin is known to have the following structure:

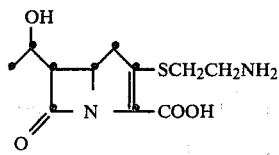

Thienamycin and all of its isomers (in pure form and as mixtures) are also obtainable by the total synthesis disclosed and claimed in co-pending, commonly assigned U.S. Patent Application Ser. No. 833,210 (Sept. 15, 1977). This application is incorporated herein by reference to the extent that it makes available all isomers of I as starting materials in the preparation of the compounds of the present invention.

The substituted N-methylene thienamycin derivatives of the present invention may be depicted by the following structural formula:

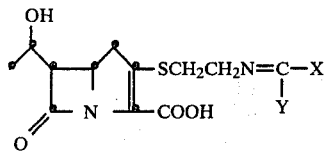

which, depending upon the basicity of the amino nitrogen (a function of the identity of the methylene substituents X and Y), may equivalently be represented as an inner salt:

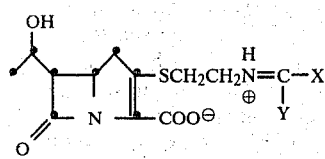

which is one canonical form of a single resonant structure, which, for example, when Y is $-NR^1R^2$ and X is R is:

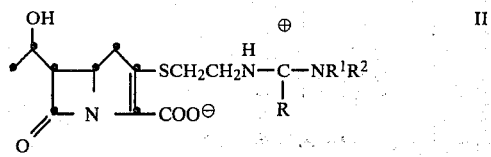

For convenience, the compounds of the present invention may be represented by the symbol:

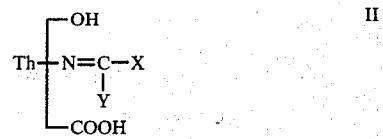

wherein "Th" indicates the bicyclic nucleus of thienamycin and its hydroxyl, amino, and carboxyl functional groups are shown; and wherein X and Y are independently selected from the group consisting of hydrogen, $-R$, $-OR$, $-SR$, and $-NR^1R^2$; $R^1$ and $R^2$ are independently selected from R, hydrogen, nitro, hydroxyl, alkoxyl having 1-6 carbon atoms, amino, mono- di- and trialkylamino wherein the alkyl moieties each comprise $1 \neq 6$ carbon atoms; $R^1$ and $R^2$ may be joined together to form a substituted or unsubstituted mono- or bicyclic heteroaryl or heterocyclyl comprising (together with the nitrogen atom to which they are attached) 4–10 atoms one or more of which may be an additional hetero atom selected from oxygen, sulphur or nitrogen; R, $R^1$ and $R^2$ are substituted or unsubstituted: cyano; carbamoyl; carboxyl; alkoxycarbonyl and alkyl having from 1 to about 10 carbon atoms; alkenyl having from 2 to about 10 carbon atoms; alkynyl having from 2 to about 10 carbon atoms; cycloalkyl having from 3 to 10 carbon atoms; cycloalkylalkyl and cycloalkylalkenyl having from 4 to 12 carbon atoms; cycloalkenyl, cycloalkenylalkenyl, and cycloalkenylalkyl having 3–10, 4–12 and 4–12 carbon atoms, respectively; aryl having from 6 to 10 carbon atoms, aralkyl, aralkenyl, and aralkynyl having from 7 to 16 carbon atoms; mono- and bicyclic heteroaryl and heteroaralkyl which typically comprise 4 to 10 ring atoms one or more of which is a hetero atom selected from oxygen, sulphur, or nitrogen and wherein the alkyl moiety of the heteroaralkyl radical comprises 1 to about 6 carbon atoms; mono- and bicyclic heterocyclyl and heterocyclylalkyl which typically comprises 4 to 10 ring atoms one or more of which is a hetero atom selected from oxygen, sulphur or nitrogen and wherein the alkyl moiety of the heterocyclylalkyl radical comprises from 1 to about 6 carbon atoms; and wherein the above-mentioned substituent or substituents on R, $R^1$, $R^2$ or on the ring formed by the joinder of $R^1$ and $R^2$, are selected from the group consisting of: halo, such as chloro, bromo, iodo and fluoro; azido;

alkyl having 1–4 carbon atoms; thio; sulpho; phosphono; cyanothio (—SCN); nitro; cyano; amino; hydrazino, mono-, di- and trialkyl substituted amino, and hydrazino wherein the alkyl has 1–6 carbon atoms; hydroxyl; alkoxyl having 1–6 carbon atoms; alkylthio having 1–6 carbon atoms; carboxyl; oxo; alkoxylcarbonyl having 1–6 carbon atoms in the alkoxyl moiety; acyloxy comprising 2–10 carbon atoms; carbamoyl and mono- and dialkylcarbamoyl wherein the alkyl groups have 1–4 carbon atoms.

The compounds of the present invention also embrace embodiments of the following structure:

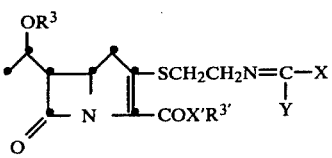
IIa which may also exist as a salt:

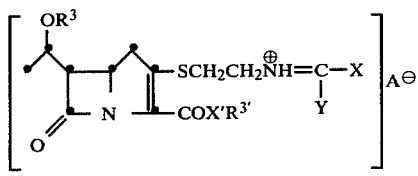
IIa or, more conveniently by the previously introduced symbol:

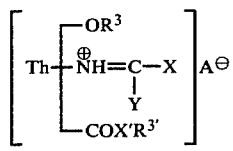
IIa wherein the non-critical counter anion, A, is representatively selected to provide pharmaceutically acceptable salts such as halides (chloro, bromo and the like), sulfate, phosphate, citrate, acetate, benzoate and the like; and $R^3$, $X'$ and $R^{3'}$ are independently selected from the groups hereinafter defined:

$X'$ is oxygen, sulphur or $NR'$ ($R'$ is hydrogen or $R^{3'}$);

$R^{3'}$ is hydrogen, or, inter alia, is representatively selected to provide the pharmaceutically acceptable salt, ester, anhydride ($R^{3'}$ is acyl), and amide moieties known in the bicyclic β-lactam antibiotic art—such moieties are enumerated in greater detail below; and $R^3$ is: (1.) acyl (generically the group $OR^3$ is classifiable as an ester); or (2.) $R^3$ is selected from alkyl, aryl, alkenyl, aralkyl and the like, such that the group $OR^3$ is generically classifiable as an ether. $R^3$ may also be hydrogen. The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl radicals, and substituted P(III and V) radicals such as substituted phosphorous-, phosphoric-, phosphonous- and phosphonic radicals. Such radicals, $R^3$, of the present invention are enumerated in greater detail below.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of thienamycin (I), but which are characterized as the substituted N-methylene derivatives thereof. These antibiotics are active against a broad range of pathogens which representatively include both gram positive bacteria such as *S. aureus, Strep. pyogenes,* and *B. subtilis* and gram negative bacteria such as *E. coli, Proteus morganii,* Klebsiella, Serratia, and Pseudomonas. Further objects of this invention are to provide chemical processes for the preparation of such antibiotics and their non-toxic pharmaceutically acceptable salt, ether, ester and amide derivatives; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (Structures II and IIa, above) may be divided into four classes:

(1.) Amidines; wherein: $Y = -NR^1R^2$ and $X =$ hydrogen or R:

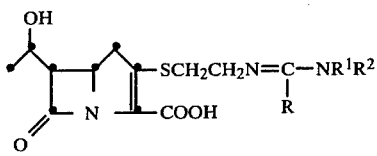

which may be represented by the resonant structure:

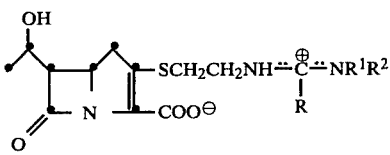

wherein R, $R^1$ and $R^2$ are as previously defined. Species IIa may similarly be depicted:

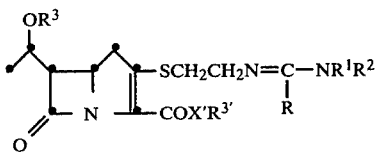

wherein $R^3$, $X'$ and $R^{3'}$ are fully defined below. Representative examples of such amidine embodiments (the substituent plus the amino group of thienamycin form the amidine structure) are:

The benzamidine: Y=—NH₂, X=phenyl;
The formamidine: Y=—NH₂, X=H;
The acetamidine: Y=—NH₂, X=CH₃;
The 4-pyridylcarboxamidine: Y=—NH₂, X=4-pyridyl;
The N-isopropyl formamidine: Y=—NHCH(CH₃)₂, X=H;
The N-methyl formamidine: Y=—NHCH₃, X=H;
The N,N-dimethylformamidine: Y=—N(CH₃)₂, X=H;
The piperidinyl methylenimine: Y=1-piperidyl, X=H.
Other preferred amidines are those wherein Y=NR¹R² and R¹ and R² are independently selected from the group consisting of: hydrogen; substituted and unsubstituted: alkyl having 1–6 carbon atoms, such as methyl, ethyl, isopropyl, butyl, t-butyl, N,N-dimethylaminoethyl, 2,2,2-trifluoroethyl, 2-methylthioethyl, and the like; alkenyl having 3–6 carbon atoms, such as allyl, methallyl, 2-butenyl, 1-buten-3-yl, and the like; cycloalkyl, cycloalkylalkyl, cycloalkenyl, and cycloalkenylalkyl having 3–6, 4–7, 4–6, and 4–7 carbon atoms, respectively, such as cyclopropyl, cyclopentyl, cyclohexyl, cyclopropylmethyl, cyclohexylmethyl, 2-cyclopropenyl, 1,4-cyclohexadienylmethyl, and the like; aralkyl and aralkenyl having 7–10 carbon atoms, such as benzyl, p-methoxybenzyl, p-dimethylaminobenzyl, cinnamyl, and the like; and monocyclic heteroaralkyl having 5–6 ring atoms, one or more of which is selected from oxygen, sulphur, and nitrogen and 1–3 carbon atoms in the alkyl moiety, such as 2-thienylmethyl, 3-thienylmethyl, 2-furylmethyl, 1-methyl-5-tetrazolylmethyl, and the like; wherein the ring or chain substituent relative to the definition of R¹ and R² may be chloro, fluoro, hydroxyl, alkoxyl having 1–3 carbon atoms, dialkylamino having 1–3 carbon atoms in each alkyl moiety, and alkylthio having 1–3 carbon atoms; X is selected from the group defined above for R and in particular is selected from the group consisting of: hydrogen; alkyl having from 1 to about 6 carbon atoms; aminoalkyl and aminoalkenyl having 1–6 carbon atoms; alkenyl having 2–6 carbon atoms; alkoxyalkyl having from 2 to about 6 carbon atoms such as methoxymethyl, ethoxyethyl and the like; mono-, di- and triloweralkylaminoalkyl having from 2 to 12 carbon atoms such as dimethylaminomethyl, methylaminomethyl, trimethylammoniummethyl and the like; perhaloalkyl having from 1 to 6 carbon atoms such as trifluoromethyl; alkylthioalkyl having from 2 to about 6 carbon atoms such as methylthiomethyl, ethylthioethyl and the like; substituted and unsubstituted: aryl and aralkyl such as phenyl and benzyl; monocyclic heteroaryl, heteroaralkyl, heterocyclyl and heterocyclylalkyl such as 2-, 3- and 4-pyridyl and 2-thiazolyl wherein the substituent or substituents are as defined above. The amidine embodiments of the present invention represent a preferred class. Further, amidine embodiments wherein X' is oxygen and R³ and R³' are hydrogen are particularly preferred.

Especially preferred amidines of the present invention are those wherein Y=—NR¹R² and X=R; wherein: R¹, R² and R are selected from hydrogen and the above-listed preferred substituted and unsubstituted: alkyl and alkenyl radicals.

(2.) Guanidines; wherein: Y=—NR¹R², and X=—NR¹R²:

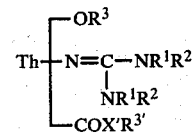

wherein all symbolism is as defined above.

Representative examples of such guanidine embodiments (the substituent plus the amino group of thienamycin form the guanidine structure) are:
The guanidine: Y=—NH₂, X=—NH₂;
The N-methylguanidine: Y=—NHCH₃, X=—NH₂;
The N,N-dimethylguanidine: Y=—N(CH₃)₂, X=—NH₂;
The N,N,N-trimethylguanidine: Y=—N(CH₃)₂, X=—NHCH₃;
The N-phenylguanidine: Y=—NH(C₆H₅), X=—NH₂;
The nitroguanidine: Y=—NHNO₂, X=—NH₂;
The aminoguanidine: Y=—NHNH₂, X=—NH₂.
Other preferred guanidines are those wherein R¹ and R² are independently selected from the group consisting of: hydrogen; substituted and unsubstituted: alkyl having 1–6 carbon atoms, such as methyl, ethyl, isopropyl, butyl, t-butyl, N,N-dimethylaminoethyl, 2,2,2-trifluoroethyl, 2-methylthioethyl, and the like; alkenyl having 3–6 carbon atoms, such as allyl, methallyl, 2-butenyl, 1-buten-3-yl, and the like; cycloalkyl, cycloalkylalkyl, cycloalkenyl, and cycloalkenylalkyl having 3–6, 4–7, 4–6, and 4–7 carbon atoms, respectively, such as cyclopropyl, cyclopentyl, cyclohexyl, cyclopropylmethyl, cyclohexylmethyl, 2-cyclopropenyl, 1,4-cyclohexadienylmethyl, and the like; aralkyl and aralkenyl having 7–10 carbon atoms, such as benzyl, p-methoxybenzyl, p-dimethylaminobenzyl, cinnamyl, and the like; monocyclic heteroalkyl having 5–6 ring atoms, one or more of which is selected from oxygen, sulphur, and nitrogen and 1–3 carbon atoms in the alkyl moiety, such as 2-thienylmethyl, 3-thienylmethyl, 2-furylmethyl, 1-methyl-5-tetrazolylmethyl, and the like; wherein the ring or chain substituent relative to the definition of R¹ and R² may be chloro, fluoro, hydroxyl, alkoxyl having 1–3 carbon atoms, dialkylamino having 1–3 carbon atoms in each alkyl moiety, and alkylthio having 1–3 carbon atoms; X' is oxygen and R³ and R³' are hydrogen.

(3.) Substituted Pseudoureas; wherein: Y=—NR¹R² and X=—OR or —SR:

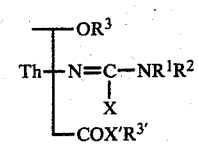

wherein R³, R³', X', R¹, and R² are as defined, and X=—OR or —SR.

Representative examples of such substituted pseudourea embodiments (the substituent plus the amino group of thienamycin form the substituted pseudourea structure) are:
The N,N-dimethyl-O-methyl pseudourea: Y=—N(CH₃)₂, X=—OCH₃;
The N,N-dimethyl-S-ethyl pseudothiourea: Y=—N(CH₃)₂, X=—SCH₂CH₃;
The N-phenyl-S-ethyl pseudothiourea: Y=—NHC₆H₅, X=—SCH₂CH₃;

The N-methyl-S-methyl pseuthiourea:
  Y=—NHCH₃, X=—SCH₃
Particularly preferred compounds are those wherein $R^3$ and $R^{3'}$ are hydrogen and $X'$ is oxygen.

(4) Imido Esters, and Imido Thioesters

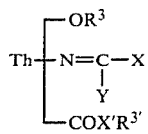

wherein $R^3$, $X'$, $R^{3'}$ and R are as defined and X is —OR or —SR and y is hydrogen, R, —OR and —SR.

Representative examples of such imido ester and imido thioester embodiments (the substituent plus the amino group of thienamycin form the imido ester or imido thioester structure) are:

The methyl formimidate:
  Y=—OCH₃, X=—H;
The S-methyl thiobenzimidate:
  Y=—SCH₃, X=phenyl;
The methyl benzyloxycarbimidate:
  Y=—OCH₃, X=—OCH₂C₆H₅;
The Diethyl dithiocarbimidate:
  Y=—S—C₂H₅, X=—S—C₂H₅.

IDENTIFICATION OF STARTING MATERIALS

The compounds of the present invention are conveniently prepared from thienamycin (I, above). Embodiments of the present invention such as IIa, above, wherein the secondary alcoholic group and/or the carboxyl group are derivatized are conveniently prepared either from the corresponding O—, carboxyl, or O— and carboxyl derivative of thienamycin or from II or thienamycin followed by subsequent reaction to establish the radicals $R^3$ and $R^{3'}$ (or —$X'R^{3'}$) and combinations thereof. Such starting materials are fully disclosed in the following U.S. Patent Applications which are incorporated herein by reference: Ser. No. 634,006 (filed Nov. 21, 1975) which is directed to O— derivatives of thienamycin (ester and ether derivatives of the secondary alcoholic group of thienamycin) and its concurrently filed continuation-in-part application Ser. No. 733,655, filed Oct. 18, 1976 having the following structural formula:

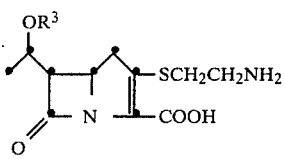

Ser. No. 634,291 (filed Nov. 21, 1975) and its concurrently filed continuation-in-part application Ser. No. 733,653, filed Oct. 18, 1976 which are directed to N-acyl derivatives of thienamycin having the following structural formula:

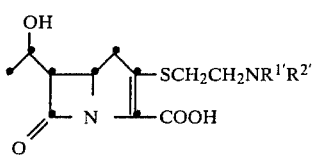

wherein $R^{1'}$ and $R^{2'}$ are selected from the group consisting of hydrogen and acyl; the term "acyl" is defined, as it is in the incorporated by reference application, below. Such N-acyl thienamycins are useful starting materials for the preparation of the substituted pseudourea (3.) and the imido ether and imido thioether (4.) embodiments of the present invention. Ser. No. 634,298 (filed Nov. 21, 1975) and its concurrently filed continuation-in-part application Ser. No. 733,651, filed Oct. 18, 1976 which are directed to carboxyl derivatives of thienamycin having the following structural formula:

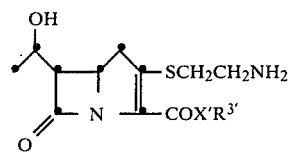

Ser. No. 634,295 (filed Nov. 21, 1975) and its concurrently filed continuation-in-part application Ser. No. 733,613, filed Oct. 18, 1976 which are directed to N-acyl and carboxyl derivatives of thienamycin having the following structural formula:

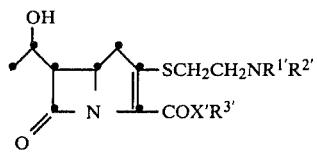

Ser. No. 634,294 (filed Nov. 21, 1975) and its concurrently filed continuation-in-part application Ser. No. 733,652, filed Oct. 18, 1976 which are directed to N-acyl, O- and carboxyl- derivatives of thienamycin having the following structural formula:

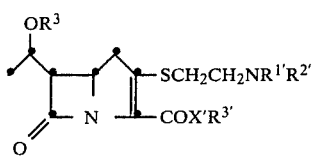

Thus embodiments of the present invention depicted as IIa, above, may be prepared by starting with the corresponding derivative Ia, Ib, Ic, Id, Ie; or embodiments IIa may be prepared directly starting with thienamycin, I, (I→II) followed by the desired derivatization procedure to establish $R^3$ and/or $X'R^{3'}$ (II→IIa) which is described in the above-cited and incorporated by reference United States Patent Applications.

Relative to structures Ia, Ib, Ic, Id, and Ie, the radicals $R^3$, $R^{3'}$, $X'$ and acyl ($R^{1'}$ and $R^{2'}$) are defined as follows:

Identification of the Radical —COX'R³'

In the generic representation of the compounds of the present invention (IIa, above), the radical represented by —COX'R³' is, inter alia, —COOH (X' is oxygen and R³' is hydrogen) and all radicals known to be effective as pharmaceutically acceptable ester, anhydride (R³' is acyl) and amide radicals in the bicyclic β-lactam antibiotic art, such as the cephalosporins and penicillins and the nuclear analogues thereof.

Suitable radicals (R³') include conventional protecting or carboxyl blocking groups. The term "blocking group" as utilized herein is employed in the same manner and in accordance with the teaching of U.S. Pat. No. 3,697,515 which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X'=O and $R^{3'}$ is given:

(i) $R^{3'} = CR^aR^bR^c$ wherein at least one of $R^a, R^b$ and $R^c$ is an electron-donor, e.g., p-methoxyphenyl, 2,4,6-trimethylphenyl, 9-anthryl, methoxy, $CH_2SCH_3$, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R^{3'} = CR^aR^bR^c$ wherein at least one of $R^a$, $R^b$ and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^{3'} = CR^aR^bR^c$ wherein at least two of $R^a$, $R^b$ and $R^c$ are hydrocarbon such as alkyl, e.g., methyl or ethyl, or aryl, e.g, phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^{3'} = R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

$R^4_3SiX'$; $R^4_2SiX'_2$; $R^4_3Si.NR^4_2$; $R^4_3Si.NH.COR^4$; $R^4_3Si.NH.CO.NH.SiR^4_3$; $R^4NH.CO.NH.SiR^4_3$; or $R^4C(OSiR^4_3)$;

$HN(SiR^4_3)_2$ wherein X' is a halogen such as chloro or bromo and the various groups $R^4$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting thienamycin or an N-protected thienamycin, such as N-acylated thienamycin, with alcohols, phenols, mercaptans, thiophenols, acylating reagents and the like. For example, esters and amides of interest are the above-listed starting materials and final products having the following group at the 2-position of the thienamycin nucleus: $-COX'R^{3'}$ wherein X' is oxygen, sulfur, or NR' (R' is H or $R^{3'}$), and $R^{3'0}$ is alkyl having 1–10 carbon atoms, straight or branched, such as methyl, ethyl, t-butyl, pentyl, decyl and the like; carbonylmethyl, including phenacyl, p-bromophenacyl, p-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1–10 and preferably 1–6 carbon atoms; but can be branched, straight or cyclic, and the alkyl portion has 1–6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1–6 carbon atoms and the alkyl portion has 1–6 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1–6 carbon atoms, e.e., 2,2,2-trichloroethyl, trifluoroethyl, 2-bromopropyl, diiodomethyl, 2-chloroethyl, 2-bromoethyl, and the like; alkenyl having 1–10 carbon atoms, either straight or branched, e.g., allyl, 2-propenyl, 3-butenyl, 4-butenyl, 4-pentenyl, 2-butenyl, 3-pentenyl, 3-methyl-3-butenyl, methallyl, 1,4-cyclohexadien-1-yl-methyl, and the like; alkynyl having 1–10 carbon atoms, either straight or branched e.g., 3-pentenyl, propargyl, ethynyl, 3-butyn-1-yl, and the like; alkanoyl, either straight or branched, having 1–10 carbon atoms, such as pivaloyl, acetyl, propionyl, and the like; aralkyl or heteroaralkyl wherein alkyl has 1–3 carbon atoms, and hetero means 1–4 hetero atoms being selected from the group consisting of O, S, or N, such as benzyl, benzhydryl, and substituted benzyl, benzhydryl, or e.g., benzyl or benzhydryl substituted with 1–3 substituents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1–4 carbon atoms chain); or phthalidyl; or phenylethyl, 2-(p-methylphenyl)-ethyl, and the arylthioalkyl analogues, aryloxyalkyl wherein aryl is preferably a phenyl ring having 0–3 substituents preferably 0 or 1 substituents in the ortho or para positions and alkyl is 1–6 carbon atoms, e.g., (4-methoxy)-phenoxymethyl, phenoxymethyl, (4-chloro)phenoxymethyl, (4-nitro)phenoxymethyl, (4-benzyloxy)phenoxymethyl, (4-methyl)-phenoxymethyl, (4-benzyloxy)phenoxymethyl, (4-methyl)phenoxymethyl, (2-methoxy)phenoxymethyl, (1-phenoxy)-ethyl, (4-amino)phenoxymethyl, (4-methoxy)phenylthiomethyl, (4-chloro)phenylthiomethyl, phenylthioethyl; aryl wherein aryl is phenyl, 5-indanyl, or substituted phenyl having 0–3 substituents, preferably 0 or 1 substituent in the ortho or para position, e.g., (4-methyl)phenyl, (4-hydroxy)-phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1–6 carbon atoms, such as 3-phenyl-2-propenyl; aralkoxyalkyl wherein aralkoxy is benzyloxy, and alkyl has 1-3 carbon atoms, such as benzylox-ymethyl, (4-nitro)benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl isopropylthioethyl, methylthiobutyl and the like.

In addition to the esters (and thio esters) listed above, amides are also embraced by the present invention, i.e., wherein X' is the

group. Representative of such amides are those wherein R' is selected from the group consisting of hydrogen, methyl, ethyl, phenyl, p-methoxyphenyl, benzyl, carboxymethyl, methylthioethyl, and heteroaryl; also embraced by —COX'R³' are anhydrides wherein R³' is acyl, for example, benzyloxycarbonyl, ethoxycarbonyl, benzoyl, and pivaloyl.

The most preferred "COX'R³' radicals of the present invention are those wherein (relative to Structure IIa above) X' is oxygen, sulphur or NR' (R' is selected from the group consisting of hydrogen and lower alkyl); and R³' is selected from the group consisting of: loweralkyl, lower alkenyl, such as methallyl, 3-methylbutenyl, 3-butenyl, and the like; methylthioethyl; benzyl and substituted benzyl such as p-t-butylbenzyl, m-phenoxybenzyl, p-pivaloyloxybenzyl, p-nitrobenzyl and the like; pivaloyloxymethyl, 3-phthalidyl and acetoxymethyl, propionyloxymethyl, acetylthiomethyl, pivaloylthiomethyl, allyl, 4-butenyl, 2-butenyl, 3-methyl-2-butenyl, phenacyl, acetoxyacetylmethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

Identification of R³ (R¹' and R²')

In the generic representation of the present invention, structure IIa (above), the radical R³ is, in addition to hydrogen, (1.) acyl (generically the group —OR³ is classifiable as an ester); or (2.) R³ is selected from alkyl, aryl, aralkyl, and the like such that the group —OR³ is classifiable as an ether. For the ester embodiments (1) R³ is selected from the following definition of acyl radicals (p=1). In the so-called ether embodiments (2.) of the present invention, R³ is selected from the same acyl radicals wherein the carbonyl moiety,

or more generally

is deleted (p=0); thus R³ is selected from the following radicals wherein all symbolism is defined below:

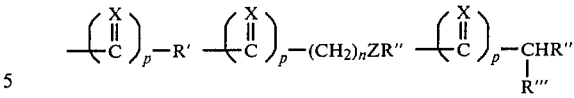

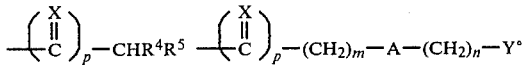

R¹' and R²' are selected from the above radicals wherein p=1. Thus, relative to the definition of R³, R¹' and R²', the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkyl-amino wherein the alkyl radical comprises 1 to about 6 carbon atoms; substituted or unsubstituted: straight or branched chain alkyl wherein the alkyl radical comprises 1 to about 6 carbon atoms; mercapto; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4 to 10 atoms and the hetero atom or atoms are selected from O, N and S; such above-listed groups can be unsubstituted or can be substituted by radicals such as OH, SH, SR (R is lower alkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4N-benzoylamino -4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)4-isoxazolyl, 4-quanidinomethylphenyl, 4-quanidinomethylbenzyl, 4-guanidinobenzyl, 4- guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)-vinyl, phenyl, o-methoxyphenyl, o-chlorophenyl, o-phenylphenyl, p-aminomethylbenzyl, 1-(5-cyanotriazolyl)-methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)methyl, 2- or 3-(5-sulfothienyl)-methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)-methyl, 3-furylmethyl, 2-thienylmethyl, 3-thienylmethyl, tetrazolylmethyl, benzamidinomethyl and cyclohexylamidinomethyl.

The acyl group can also be a radical of the formula:

—C(CH$_2$)$_n$ZR'' wherein X is O or S and n is 0–4, Z represents oxygen, sulfur, carbonyl or nitrogen and R'' is defined as above. Representative members of the substituent —(CH$_2$)$_n$ZR'' that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxyethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl, and 1-pyrrolobutyl.

Alternatively, the acyl group can be a radical of the formula:

wherein R'' is defined as above and R''' is a radical such as amino, hydroxy, azido, carbamoyl, guanidino, ureamidino, acyloxy, halo, such as Cl, F. Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3-or 4-hydroxybenzyl, α-amino-2,4-dichlorobenzyl, α-amino-3,4-dichlorobenzyl, D(-)-α-hydroxybenzyl, α-carboxybenzyl, α-amino-(3-thienyl)methyl D(-)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(-)-2-thienyl-guanidinomethyl, D(-)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl, 3-(1,2-thiaziolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)carboxymethyl, 2-benzothienylaminomethyl, 2-benzothienylhydroxymethyl, 2-benzothienylcarboxymethyl, α-sulfobenzyl, α-phosphonobenzyl, α-diethylphosphono, and α-monoethylphosphono. Further acyl radicals of interest in this class when X=oxygen are:

wherein R$^4$ and R$^5$ are as defined below. R$^4$ represents hydrogen, halo, such as chloro, fluoro, bromo, iodo, amino, guanidino, phosphono, hydroxy, tetrazolyl, carboxy, sulfo, or sulfamino and R$^5$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and and the like substituted heterocycles, phenylthio, phenyloxy, lower alkyl of 1–6 carbon atoms, heterocyclic or substituted heterocyclic thio groups; or cyano. The substituents on the moieties, R$^4$ and R$^5$, can be halo, carboxymethyl, guanidino, guanidinomethyl, carboxamidomethyl, aminomethyl, nitro, methoxy or methyl. When R$^4$ is selected from the group consisting of hydrogen, hydroxy, amino or carboxy and R$^5$ is selected from the group consisting of phenyl, or a 5—or 6-membered heterocyclic ring having one or two sulfur, oxygen or nitrogen hetero atom such as tetrazolyl, thienyl, furyl and phenyl, the following acyl radicals are representative: phenylacetyl 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3- methyl-1,2,5-thiadiazolylacetyl, 3-chloro-B 1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-theinylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorous (2) radicals:

wherein with respect to 1, m and n are integers selected from 0 or 1 and Y°=O⊖M⊕, —N(R'')₂, and R''; wherein M⊕ is selected from hydrogen, alkali metal cations and organic bases; and R'' is as defined above, e.g., alkyl, alkenyl, aryl and heteroaryl. With respect to 2 X=O or S; n=0 or 1; and y' and —N(R'')₂, R'' and ZR'' wherein all symbolism is as defined above, e.g., R'' and ZR'' are representatively: alkyl, alkenyl, aryl, heteroaryloxy, Y' and Y'', including R'' moieties, can be joined together to form cyclic ester, ester-amide and amide functions. Illustrative examples of 1 are O-(methylsulphonyl)-theinamycin, O-(p-nitrophenylsulphonyl)thienamycin, O-(p-chlorophenylsulphinyl)thienamycin, O-(o-nitrophenylsulphenyl)thienamycin, O-sulfamoylthienamycin, O-dimethylsulphamoylthienamycin and thienamycin O-sulphonic acid sodium salt. Illustrative examples of 2 are O-(dimethoxyphosphino)thienamycin, O-(dibenzyloxyphosphino)-theinamycin, O-(dihydroxyphosphino)thienamycin disodium salt, O-(dimethoxyphosphinyl)thienamycin, O-(dimethoxyphosphinothioyl)thienamycin, O-(dibenzyloxyphosphinyl)-thienamycin, and O-(dihydroxyphosphinyl)thienamycin disodium salt. The definition of R¹' and R²' does not embrace radicals 1 and 2.

An acyl class of particular interest in those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as trilower alkyl silyl, for example, trimethylsilyl and t-butyldimethyl are also of interest.

The following radicals, according to the foregoing definition of acyl, are especially preferred for R³ of structure IIa: formyl, acetyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylamino-acetyl, N,N,N,-trimethylaminoacetyl, 3-(N,N-dimethyl)amino-propionyl, 3-(N,N,N-trimethyl)aminopropionyl, N,N,N-triethylaminoacetyl, pyridiniumacetyl, guanidinoacetyl, 3-guanidinopropionyl, N³-methylguanidinopionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, N³-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl, sulfo, phosphono,

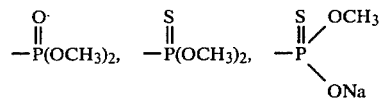

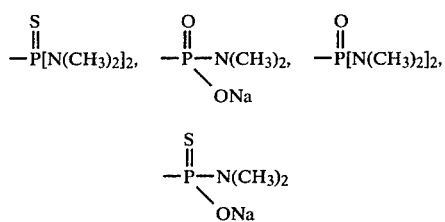

Another class of acyl radicals are terminally substituted acyls wherein the substituent is a basic group such as substituted and unsubstituted: amino, amidino, guanidino, guanyl and nitrogen-containing mono- and bicyclic heterocyles (aromatic and non-aromatic) wherein the hetero atom or atoms, in addition to nitrogen, are selected from oxygen and sulphur. Such substituted acyls may be represented by the following formula:

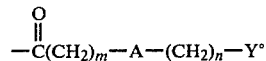

wherein m, and n are integers selected from 0 to 5; A is O, NR' (R' is hydrogen or loweralkyl having 1-6 carbon atoms), S or A represents a single bond; and Y° is selected from the following group:

(1.) amino or substituted amino:

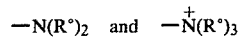

wherein the values for R° are independently selected from: hydrogen; N(R')₂ (R' is hydrogen or loweralkyl having 1-6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2–6 carbon atoms; cycloalkyl and cycloalkylalkyl wherein the cycloalkyl moiety comprises 3-6 carbon atoms and the alkyl moiety comprises 1-3 carbon atoms, two R° groups may be joined together with the N atom to which they are attached to form a ring having 3-6 atoms.

(2.) amidino and substituted amidino:

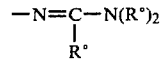

wherein the value of R° is independently selected from the group consisting of: hydrogen, N(R')$_2$ (R' is hydrogen or loweralkyl having 1–6 carbon atoms); loweralkyl and loweralkoxyl having from 1 to 6 carbon atoms, loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R° groups may be joined together with the atoms to which they are attached to form a ring having 3 to 6 atoms;

(3.) guanidino and substituted guanidino:

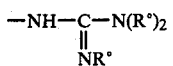

wherein R° is as defined in 2.(above).

(4.) guanyl and substituted guanyl:

wherein R° is as defined in 2. (above).

(5.) nitrogen-containing mono- and bicyclic heterocyclyls (aromatic and non-aromatic) having 4 to 10 nuclear atoms wherein the hetero atom or atoms, in addition to nitrogen, are selected from oxygen and sulphur. Such heterocyclyls are representatively illustrated by the following list of radicals (R' is H or loweralkyl having 1–6 carbon atoms):

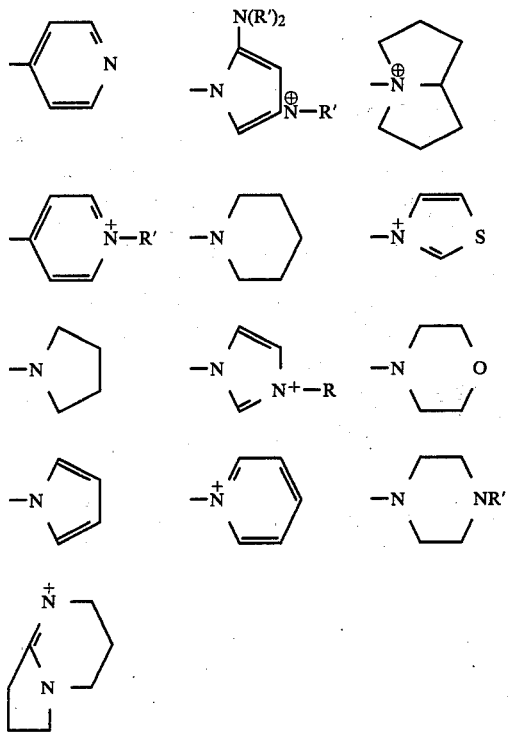

The following specific acyl radicals falling within this class are additionally representative:

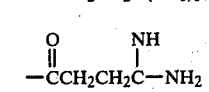
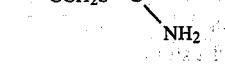
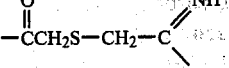

Preparation of Starting Materials Ia, Ib, Ic, Id and Ie

The above-described starting materials are conveniently prepared from an N-protected thienamycin (1), such as an N-acylated thienamycin (1).

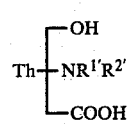

wherein R$^{1'}$ and R$^{2'}$ are selected from hydrogen and the above-defined acyl radicals. Preferably R$^{1'}$ is hydrogen and R$^{2'}$ is an easily removable blocking group such as: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl, and t-butyldimethylsilyl are also of interest. The most preferred N-blocking groups are the substituted and unsubstituted carbobenzyloxy radical:

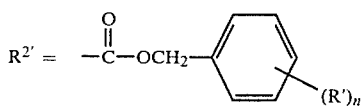

wherein n is 0-2 (n=0, R'=hydrogen) and R' is lower alkoxy or nitro; and bromo-t-butoxycarbonyl,

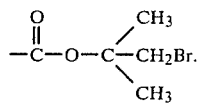

The ultimate N-deblocking procedure for the preparation of Ia, Ic or Ie is accomplished by any of a variety of well-known procedures which include hydrolysis or hydrogenation; when hydrogenation is employed suitable conditions involve a solvent such as a loweralkanol in the presence of a hydrogenation catalyst such as palladium, platinum or oxides thereof.

The N-acylated intermediate [1,(or Ia) above] is prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester.

Such N-acylated thienamycin starting materials are fully described in co-pending, concurrently filed U.S. Patent Application Ser. No. 634,291 filed Nov. 21, 1975 and in its continuation-in-part U.S. Patent Application Ser. No. 733,653, filed Oct. 18, 1976. These applications are incorporated herein by reference.

The acylation reaction may be conducted at a temperature in the range of from about $-20°$ to about $100°$ C., but is preferably conducted at a temperature in the range of from $-9°$ C. Any solvent in which the reactants are soluble and substantially inert may be employed, for example polar solvents such as water, alcohols and polar organic solvents in general such as dimethylformamide (DMF), hexamethyl, phosphoramide (HMPA), acetone, dioxane tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

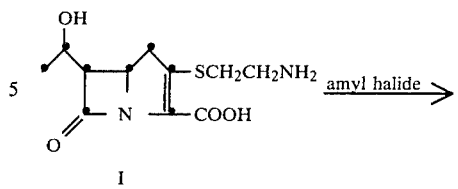

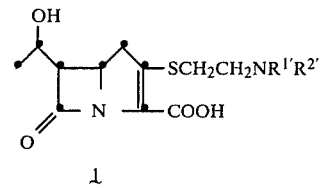

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, MgO, NaOH, $K_2HPO_4$ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin proceeds rapidly to give the tris-triorganosilyl derivative, for example tris-trimethylsilyl thienamycin $Th(TMS)_3$:

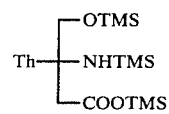

Such derivatives, which are readily soluble in organic solvents, are conveniently prepared by treating thienamycin with an excess of hexamethyldisilazane and trimethylchlorosilane at $25°$ C., with vigorous stirring under a $N_2$ atmosphere. The resulting $NH_4Cl$ is removed by centrifugation and the solvent is removed by evaporation to provide the desired silyl derivative.

The intermediate starting materials Ic are prepared according to the following scheme; however, it should be noted that direct esterification, without protection of the amino group, is also possible.

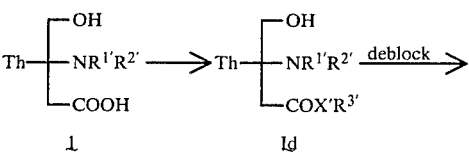

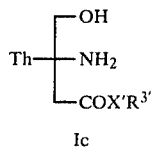

wherein all symbolism is as previously defined.

In general, the transformation (1→Ic) is accomplished by conventional procedures known in the art. Such procedures include:

(1.) Reaction of 1 (or I) with a diazoalkane such as diazomethane, phenyldiazomethane, diphenyldiazomethane, and the like, in a solvent such as dioxane, ethylacetate, acetonitrile and the like at a temperature of from 0° C. to reflux for from a few minutes to 2 hours.

(2.) Reaction of an alkali metal salt of 1 with an activated alkyl halide such as methyliodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C. to 60° C. for from a few minutes to 4 hours.

(3.) Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from 0° C. to reflux for from 15 minutes to 18 hours, include $CHCl_3$, $CH_3Cl$, $CH_2Cl_2$ and the like.

(4.) Reaction of an N-acylated acid anhydride of 1 prepared by reacting the free acid 1 with an acid chloride such as ethylchloroformate, benzylchloroformate and the like, with an alcohol such as those listed in (3.) under the same conditions of reaction as given above for (3.). The anhydride is prepared by reacting 1 and the acid chloride in a solvent such as tetrahydrofuran (THF), $CH_2Cl_2$ and the like at a temperature of from 25° C., to reflux for from 15 minutes to 10 hours.

(5.) Reaction of labile esters of 1 such as the trimethylsilyl ester, dimethyl-t-butylsilyl ester or the like with $R^{3'}X°$ wherein $X°$ is halogen such as bromo and chloro and $R^{3'}$ is as defined, in a solvent such as THF, $CH_2Cl_2$ and the like at a temperature of from 0° C. to reflux for from 15 minutes to 16 hours. For example according to the following scheme:

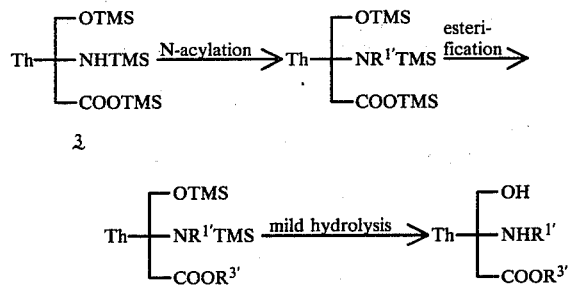

2 wherein TMS is triorganosilyl such as trimethylsilyl and all other symbolism is as previously defined.

The amides of the present invention are most conveniently prepared by reacting the acid anhydride (Ic, X'=O, $R^{3'}$=acyl) with ammonia or with the amine of choice, e.g., the alkyl-, dialkyl-, aralkyl- or heterocyclic amines listed above.

The above-recited schemes of esterification are well known in the related bicyclic β-lactam antibiotic art and indeed in all of general organic synthesis and it is to be noted that there is no undue criticality of reaction parameters in the preparation of the N-acylated and carboxyl derivatives Ic useful as starting materials in the practice of the present invention.

Starting materials Ia and Ie are conveniently prepared by any of a variety of well-known esterification or etherification reactions upon the secondary alcoholic group of Id. Such procedures include:

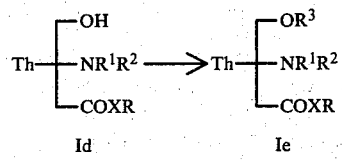

(1.) For the preparation of ether embodiments of the present invention, the acid catalized reaction of Id with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from −78° C. to 25° C. for from a few minutes to 2 hours.

(2.) For the preparation of ether embodiments of the present invention, the reaction of Id with an alkylating agent such as active halides, for example methyliodide, benzylbromide, m-phenoxybenzylbromide and the like; alkylsulphonates such as dimethylsulphate, diethylsulphate, methylfluorosulphonate and the like in the presence of a strong base capable of forming the alcoholate anion of Ib. Suitable bases include alkali and alkaline earth metal oxides and hydrous oxides, alkali metal alkoxides such as potassium, tertiarybutoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from −78° C. to 25° C., for from a few minutes to 4 hours.

(3.) For the preparation of ester embodiments, of the present invention, the reaction of Id with any of the above-listed acyl radicals in their acid form. This reaction may be conducted in the presence of a carbodiimide condensing agent such as dicyclohexylcarbodiimide or the like. Suitable solvents include any inert solvent such as $CHCl_3$, $CH_2Cl_2$, DMF, HMPA, acetone, dioxane and the like at a temperature of from 0° C. to 60° C. for from 15 minutes to 12 hours.

(4.) For the preparation of ester embodiments of the present invention, the reaction of Id with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylamine, pyridine, and the like at a temperature of from 0° C. to 40° C. for from 1 to 4 hours.

Suitable acyl halides and anhydrides include: acetic anhydride, bromoacetic anhydride, propionic anhydride, benzoylchloride, phenylacetyl, chloride azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, methanesulfonyl chloride, dibenzylphosphorochloridate, dimethylthiophosphorochloridate, 2-furoyl ethyl carbonic anhydride, methylchloroformate, bis(p-nitrobenzyl)phosphorochloridate and the like.

(5.) For the preparation of ester embodiments of the present invention, the reaction of Id with a suitably substituted ketene or isocyanate such as ketene, dimethyl ketene, methylisocyanate, methylisothiocyanate, chlorosulfonyl isocyanate and the like. Suitable solvents include dioxane, tetrahydrofuran, chloroform and the like at a temperature of from −70° C. to 60° C. for from 15 minutes to 18 hours.

The intermediate Ie is then N-deblocked as described above to provide starting materials, Ie ($R^{1'}$ and $R^{2'}$=H) and Ia. From Ie, Ia is prepared by deblocking the carboxyl group:

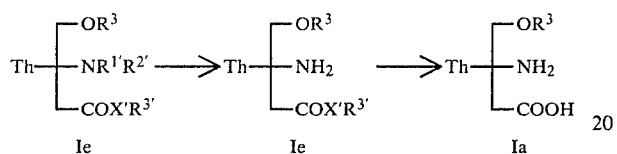

Starting material Ia is conveniently and preferably obtained when X' is oxygen and $R^{3'}$ is a readily removable carboxyl protecting or blocking group (see above). Starting material Ia is prepared by deblocking according to any of a variety of well known procedures which include hydrolysis and hydrogenation. When the preferred carboxyl-blocking groups are employed (below), the preferred deblocking procedure is hydrogenation, wherein the intermediate species (Ie) in a solvent such as a lower alkanol, is hydrogenated in the presence of a hydrogenation catalyst such as palladium, platinum or oxides thereof.

In this connection, it is noted that suitable "blocking groups" $R^{3'}$ include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" $R^{3'}$ include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

The preferred carboxyl blocking groups, are benzyl and substituted benzyl:

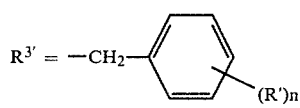

wherein n is 0–2 (n=0, R'=H) and R' is loweralkoxy or nitro.

In the alternative it should be noted that the compounds of the present invention, IIa, may be arrived at by operating upon the substituted N-methylene thienamycin derivatives, II, to achieve derivatization by establishment of $R^3$ and/or —COX'$R^{3'}$. Such procedure is exactly as described above except that species II replaces the above-described starting materials, such as Ia, Ic and Ie, and, of course, there is no need to N-deblock.

Preparation

The preparation of the compounds of the present invention is conveniently described according to the above-defined four classes, or embodiments, namely: (1.) Amidines; (2.) Guanidines; (3.) Substituted Pseudoureas; and (4.) Imido Esters, and Imino Thioesters.

(1.) Amidines. In general, the compounds of Class (1.) may conveniently be prepared by reacting thienamycin (I) or a derivative thereof (Ia, Ic or Ie, where $R^{1'}=R^{2'}=H$) or a suitably protected form of thienamycin such as its silylated derivative (1) with an imido ester (a.) or a substituted imido halide (b.):

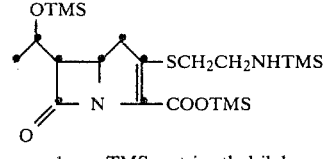

1    TMS = trimethylsilyl

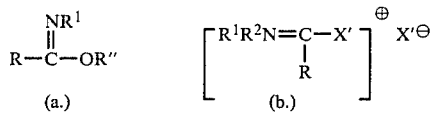

wherein $R^1$, $R^2$, and R are as defined above; X' is halo such as chloro; and —OR" is a leaving group wherein R" is loweralkyl such as methyl, ethyl and the like. Alternatively, the compounds of Class 1 may be prepared by reacting a compound of Class 4. with NH$_3$ or a primary or secondary amino compounds (c.) calculated to provide the desired species of Class 1. Reagents a., b., and c., are representatively enumerated below.

Suitable solvents for the preparation of the compounds of Class 1 according to the above reaction schemes, depending upon the identity of the thienamycin substrate and reagent, include water, dioxane, tetrahydrofuran (THF), dimethylformamide (DMF), chloroform, acetone, acetonitrile or mixtures thereof. The reaction is conducted at a temperature of from 0° to about 25° C. for from 1 to about 6 hours. There is no criticality as to the precise identity of the reaction solvent nor the variables of reaction within the limits described above, provided only that the reaction solvent is inert or substantially inert to the intended course of reaction. Suitable reagents representatively include:

(a.) Imido Esters:

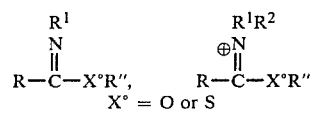

Methyl formimidate, ethyl formimidate, methyl acetimidate, ethyl acetimidate, methyl benzimidate, ethyl 4-pyridyl carboximidate, methyl phenylacetimidate, methyl 3-thienylcarboximidate, methyl azidoacetimidate, methyl chloroacetimidate, methyl cyclohexylcarboximidate, methyl 2-furylcarboximidate, methyl p-nitrobenzimidate, methyl 2,4-dimethoxybenzimidate, ethyl N=methyl formimidate, methyl N-methyl formimidate, methyl N-isopropyl formimidate, and the like.

Such imido ester reagents (a.) are conveniently prepared by any of a variety of known procedures, such as:

(1.) The reaction of a nitrile, RCN, with a lower alkanol in the presence of HCl according to the well-known Pinner synthesis.

(2.) The reaction of a nitrile, RCN, with a lower alkanol in the presence of a base. Typically, the reaction is conducted at 0°–40° C. in the presence of an excess of the alcohol with a catalytic amount of an alkali-metal alkoxide for from 15 minutes to 4 hours.

(3.) The reaction of an amide,

RCNHR$^1$, with an alkylchloroformate, such as methylchloroformate at 25° C.–45° C. for 1–4 hours.

(4.) The reaction of an N-substituted amide,

RCNHR$^1$ or RCNR$^1$R$^2$, with an equivalent of an alkylating agent such as triethyloxonium fluoroborate in an inert solvent such as ether, chloroform or the like at 0°–23° C. for from 10 minutes to 2 hours.

(5.) The conversion of a readily available imido ester,

RCNR'
|
OR''

(R' may be hydrogen), to a desired imido ester,

RCNR$^1$,
|
OR'' by reaction of the first-mentioned with an alkylamine, R$^1$NH$_2$, in a mixture of water and an immiscible solvent such as ether or chloroform at 0°–23° C. for from 5 minutes to 1 hour.

(b) Substituted Imidoyl Halides:

Chloropiperidino methylium chloride, chlorodimethylforminium chloride, chlorodiethylforminium chloride, and the like.

Such imidoyl halide reagents (b.) are conveniently prepared by any of a variety of known procedures, such as:

(1.) The reaction of an N,N-disubstituted amide,

RCNR$^1$R$^2$, with a halogenating agent such as thionyl chloride, phosgene, phosphorous pentachloride or the like in an inert solvent such as chloroform, methylene chloride and the like at 0°–40° C. for from 1–5 hours.

(c.) Primary and Secondary Amino Compounds:

Methylamine, ethylamine, 2-aminopyrimidine, dimethylamine, methyl benzylamine, 3-aminoethyl pyridine, 2-aminomethyl thiopene, ethanolamine, dimethylaminoethylamine, N-2-(aminoethyl)pyrrolidine, cyclohexylamine, n-heptylamine, isopropylamine, 2-methylallylamine, 3-phenyl-1-propylamine, 2-amino-4-picoline, 2-amino pyridine, 3-amino-4-carbethoxypyrazole, 2-aminothiazole, 5amino-3-methyl isothiazole, and 3-amino-1,2,4-triazole.

The reaction involving the reagents (a.), may be representatively shown by the following diagram:

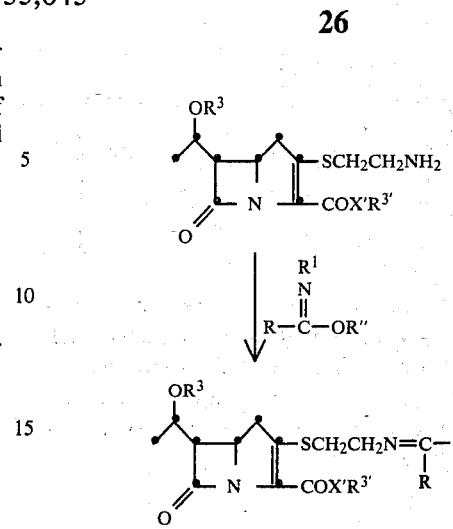

wherein OR'' is the leaving group of the imido ester reagent and R, R$^1$, R$^{3'}$, R$^3$ and X' are as defined above. This reaction is particularly suitable for embodiments wherein R$^3$ and R$^{3'}$ are hydrogen and X' is oxygen.

The reaction involving the reagents, (b.), may representatively be shown by the following diagram:

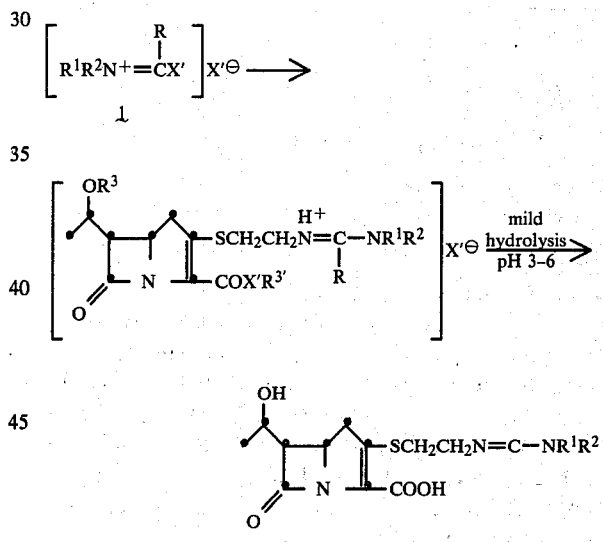

wherein all symbolism is as previously defined. When product 2 is desired, suitable values for R$^3$ and R$^{3'}$ are trimethylsilyl and X' is oxygen.

The reaction involving the reagents, (c.), may representatively be shown by the following diagram:

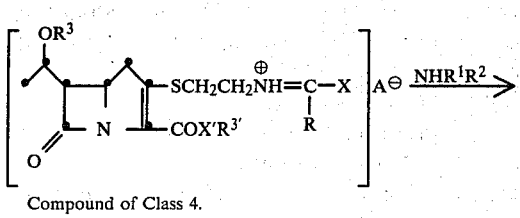

Compound of Class 4.

-continued

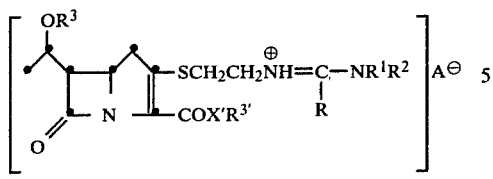

wherein all symbolism is as previously defined and X is —OR or —SR wherein R is preferably lower alkyl such as methyl or ethyl. When $R^3$ and $R^{3'}$ are readily removable blocking or protecting groups they may independently be removed by well known procedures to provide species 3, 4 and 5.

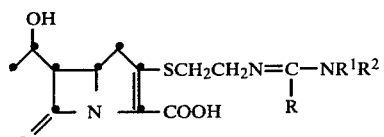

3

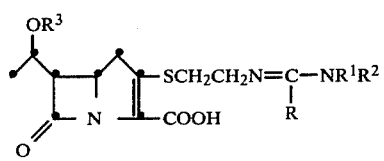

4

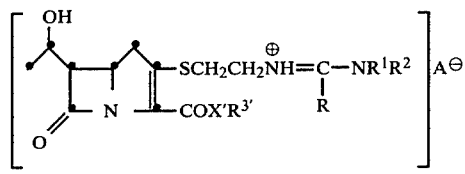

5

(2.) Guanidines:

In general, the compounds of Class 2, may conveniently be prepared by reacting thienamycin or an O- or carboxyl derivative thereof (Ia,Ic or Ie, when $R^{1'} = R^{2'} = H$) with (a.) an —OR" (e.g., O-alkyl, O-aryl) pseudourea or an S-alkyl or S-aryl pseudothiourea; or (b.) by reacting a compound of Class 3. (above) with ammonia or an amino compound such as an alkyl, aralkyl or heteroaralkyl amine.

Suitable solvents for such reactions include water and buffered aqueous polar organic solvent mixtures at pH 7-9 or anhydrous polar organic solvents such as dimethylformamide or hexamethylphosphoramide at a temperature of from 0° C. to 40° C. for from 1 to 24 hours.

Suitable reagents, (a.) and (b.), include:

(a.) —OR pseudoureas and —SR pseudothioureas:

O-Methyl pseudourea, S-Methylpseudothiourea, S-methylpseudothionitrourea, O-2,4-dichlorophenyl pseudourea, S-p-nitrophenyl pseudothiourea, O-N,N-trimethylpseudourea, and the like.

(b.) Amino reagents:

These reagents are the same as those given for the preparation of Class 1 (c.), above.

The reaction involving the reagents, (a.), may representatively be shown by the following diagram:

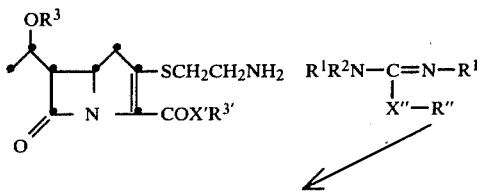

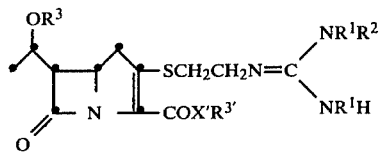

wherein $R^3$, X', $R^{3'}$, $R^1$ and $R^2$ are as defined above; X" is O or S and R" is as defined and preferably is lower alkyl or aryl.

The reaction involving the reagents, (b.), may representatively be shown by the following diagram:

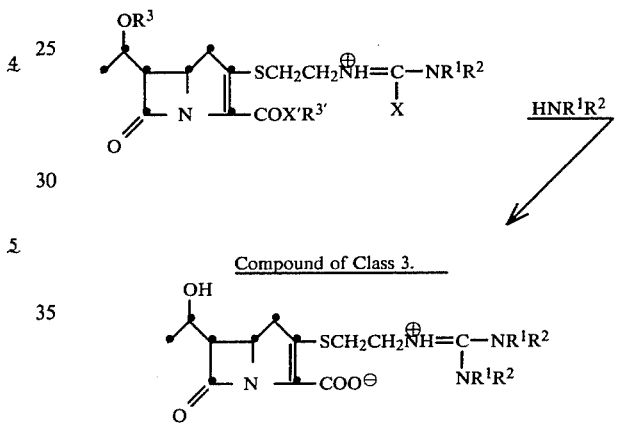

wherein all symbolism is as previously defined.

(3.) Substituted Pseudoureas:

In general, the compounds of Class 3. May conveniently be prepared by reacting a carbamyl or thiocarbamyl N-substituted Thienamycin species (a.), for example:

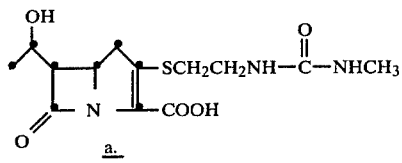

or

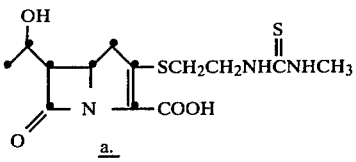

with an alkylating agent (b.) such as an active alkyl or aralkyl halide or sulfate ester.

Suitable solvents for the above reaction include lower alkanols, dioxane and acetonitrile at a temperature of from 20° C. to 60° C. for from 1 to 4 hours.

Suitable reagents (a.) for above reaction scheme include N-acyl Thienamycins:

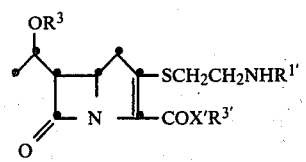
a.

wherein $R^3$, $X'$ and $R^{3'}$ are as defined above and $R^{1'}$ is acyl as defined above and preferably is selected from the group consisting of:

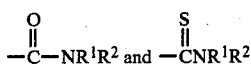

$R^1$ and $R^2$ are as defined above), such as: carbamyl, methylcarbamyl, ethylcarbamyl, phenylcarbamyl, p-bromophenylcarbamyl, phenylthiocarbamyl, methylthiocarbamyl, dimethylcarbamyl, and the like.

Suitable reagents (b.), alkylating agents, include: methyl iodide, benzyl bromide, dimethylsulfate, diethylsulfate, allyl bromide, 2-thienyl bromide, methallyl bromide, p-nitrobenzyl bromide, methyl chloromethyl ether, and the like.

The reaction involving the above reagents (a.) and (b.) may representatively be shown by the following diagram:

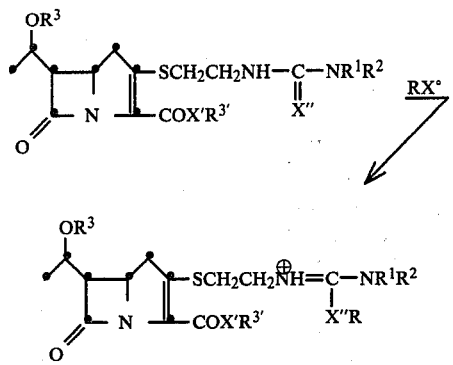

wherein $X''$ is O or S; $X°$ is halogen such as bromo, iodo or alkyl sulphate; $RX°$ is the alkylating agent; and $R^1$, $R^2$, $R^3$, $X'$, $R^{3'}$ and R are as previously defined.

(4.) Imido Esters and Imido Thio Esters:

In general, the compounds of Class 4. may conveniently be prepared by reacting a suitably protected N-acyl, N-thioacyl or N-alkoxy carbonyl derivative of thienamycin (a.) with an alkylating agent (b.).

Suitable solvents for the above reaction include methylene chloride, tetrahydrofuran, dioxane, chloroform, and the like at a temperature of from −78° C. to 25° C. for from 5 minutes to 3 hours.

Suitable N-acyl thienamycin starting materials (a.) include:

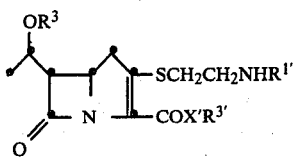

wherein $R^{1'}$ is acyl such as formyl, benzoyl, thiobenzoyl, thioacetyl, and the like; $R^3$, $R^{3'}$ and $X'$ are as defined.

Suitable alkylating agents, (b.) include: triethyl oxonium fluoroborate, methyl fluorosulphonate, and trimethyloxonium hexafluorophosphate.

The reaction involving the above reagents (a. and b.) may representatively be shown by the following diagram:

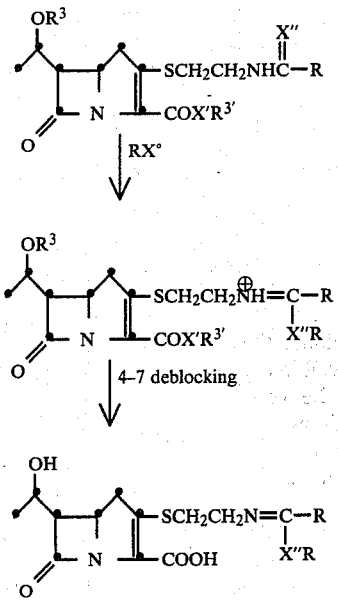

wherein $X''$=O or S; and $R^3$, $X'$, $R^{3'}$ and R are as previously defined. When the deblocked species is desired suitable values for $X'$ and $R^3$, $R^{3'}$ are oxygen and trimethylsilyl; in which case, deblocking is conveniently achieved by mild aqueous hydrolysis of pH 3-6. It is to be noted that the above reaction mixture may be used directly in reaction with the amine (c.) as described in the preparation of the amidines of Class 1, above.

The products of this invention (II and IIa) form a wide variety of pharmacologically acceptable salts such as acid addition salts, e.g., with hydrochloric, hydrobromic, sulfuric, nitric, toluene-p-sulphonic and methane sulphonic acids. The salts of this invention are pharmacologically acceptable non-toxic derivatives which can be used as the active ingredient in suitable unit-dosage pharmaceutical forms. Also, they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae, Serratia, Salmonella typhosa, Pseudomonas* and *Bacterium proteus.* The anti-bacterials of the invention may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methylcellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10-60%. The composition will generally contain from about 15 mg. to about 1500 mg. of the active ingredient; however, in general, it is preferable to employ a dosage amount in the range of from about 100 mg. to 1000 mg. In parenteral administration the unit dosage is usually the pure compound in a slightly acidified sterile water solution or in the form of a soluble powder intended for solution.

The following Examples, illustrate but do not limit the product, process, compositional or method of treatment aspects of the present invention. In the Examples, the thienamycin nucleus (I, above) is represented by the following symbol:

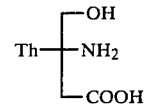

wherein the secondary alcoholic group, the amino group and the carboxyl group are illustrated. Thus, compounds of the present invention can conveniently be represented as follows:

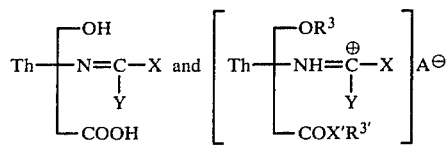

wherein X, Y, R³, X', R³' and A are as previously defined. All temperatures are in °C.

EXAMPLE 1

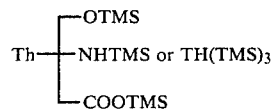

TMS = trimethylsilyl

Preparation of Silylated-Thienamycin

Thienamycin (80.0 mg.) is suspended in 40 ml. tetrahydrofuran (THF) under a N₂ atmosphere and is concentrated to 10 ml.; hexamethyldisilazane (1.0 ml.) and trimethylchlorosilane (300 μl) is added. The mixture is reacted for 20 mins. at 25° C. with vigorous stirring.

The suspension is then centrifuged to remove ammonium chloride. The supernatant is evaporated to an oil under a nitrogen stream for future reaction.

EXAMPLE 1a

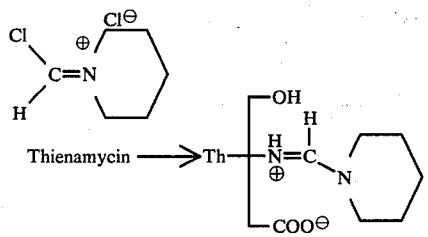

Preparation of Thienamycin N-Piperidin-1-yl Methylene Derivative

Thienamycin (57 mg., 162 μmol) is silylated according to the procedure previously described. The silylated antibiotic Th(TMS)$_3$, is dissolved in methylene chloride (6 cc) in a septum stoppered flask under positive nitrogen pressure and cooled in a dry ice-acetone bath. To the magnetically stirred solution is added a solution (180 μl) of triethylamine (644 μmol) in methylene chloride. This is followed by the addition of a solution of chloropiperidinomethylium chloride (67 mg., 405 μmol) in methylene chloride (465 μl). After 1 hour in the dry ice bath, the reaction solution is rapidly added to a tetrahydrofuran—pH 7, 0.1 N phosphate buffer (1:1) solution (50 ml.). The mixture is then concentrated under vacuum to 10 ml. to give a homogeneous solution. The solution is washed twice with ethyl acetate (2×5 ml.) and ether (2×5 ml.) and briefly pumped under vacuum. This aqueous solution is then chromatographed on an XAD-2 resin column (60 ml. bed). The product is eluted in 10% aqueous tetrahydrofuran (following water elution) to give 12.9 mg. (22%) product (as measured in solution assuming $\epsilon 8,030$ ($\lambda$max.=298 nm) same as thienamycin. Paper chromatography $R_f$ 0.42 (4:1:5, n-BuOH:EtOH:water).

EXAMPLE 2

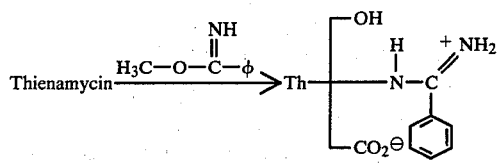

Preparation of N-Benzimidoyl Thienamycin

Thienamycin (59 mg., 212 μmol) is dissolved in a 33% N,N-dimethylformamide pH 7 phosphate buffer (0.05 N) solution (4.5 ml.) and adjusted to pH 9.5 using 2.5 N NaOH with an automatic dispensing burette. The solution is magnetically stirred at 25° C. and methylbenzimidate.HCl (340 mg., 1981 μmol) is added at once. After 30 min. the solution is extracted twice with an equal volume of chloroform and adjusted with dilute aqueous phosphoric acid to pH 7.0. The buffered solution is chromatographed on XAD-2 resin (65 ml.). The column is first eluted with water followed by 10% aqueous tetrahydrofuran which elutes the product. This fraction is concentrated to one-half volume and freeze-dried to give 50 mg. of the product. Electrophoretic mobility (50 V/cm., 20 min., pH 7 0.1 N phosphate buffer) is 1.5 cm. towards the anode. UV$\lambda_{max}$=300 nm ($\epsilon$6,960) pH 7 0.1 N phsophate buffer.

EXAMPLE 3

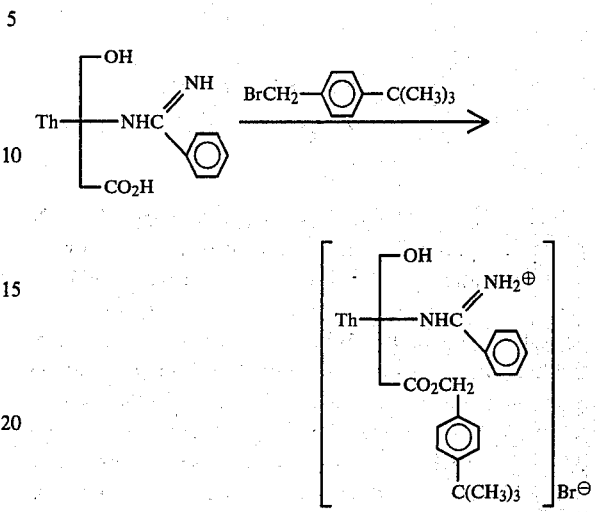

Preparation of N-Benzimidoyl Thienamycin, p-tert-Butylbenzyl Ester

Benzimidoyl Thienamycin (3.2 mg.) is suspended in hexamethylphosphoramide (75 μl.) containing p-tert-butylbenzyl bromide (3.8 μl) and magnetically stirred at 22° C. After 45 minutes a solution results which is stirred an additional hour. The product is then precipitated out of solution with ether and the crude product chromatographed on a 250μ thick silica gel plate developed in 7:3, chloroform-ethanol. The band at $R_f$0.6 is removed and eluted with ethanol to give N-benzimidoyl thienamycin, p-tert-butylbenzyl ester hydrobromide. Mass Spec. m/e 521 (M+), 487, 444, 418, 341, 323, 297, 226, 147.

EXAMPLE 4

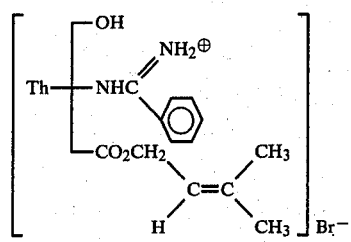

Preparation of N-Benzimidoyl Thienamycin, 3-Methyl-2-Buten-1-yl Ester

Benzimidoyl thienamycin (5.9 mg.) is dissolved in hexamethylphosphoramide (100 μl.) containing 1-bromo-3-methyl-2-butene (4.8 μl.) and triethylamine (0.5 μl.) and magnetically stirred at 22° C. After 1 hour the crude reaction is chromatographed on a 250μ thick silica gel plate developed in 8:2, chloroform, ethanol. The band of $R_f$0.1–$R_f$0.3 is removed and eluted with ethanol. Benzimidoyl thienamycin, 3-methyl-2-buten-1-yl ester hydrobromide is isolated as a solid after precipitation from an ethanol-chloroform solution with hexane.

EXAMPLE 5

Preparation of N-Formimidoyl Thienamycin

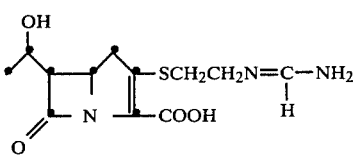

Thienamycin (517 mg) is dissolved in pH 7 0.1 N phosphate buffer (25 ml) and cooled in an ice bath with magnetic stirring. The solution is adjusted to pH 8.5 using 2.5 N sodium hydroxide solution dispensed from an automatic burette. While maintaining a pH of 8.5, methyl formimidate hydrochloride (711 mg) is added portionwise over 2–3 minutes. After an additional 10 minutes, the pH of the solution is brought to 7.0 using 2.5 N hydrochloric acid. The solution is chromatographed on a column of XAD-2 resin (150 cc) which is eluted with water. The N-formimidoyl thienamycin derivative elutes in 1.5–2.0 column volumes (200–300 cc) and is lyophilized to a white solid (217 mg). UV (pH 7 0.1 N phosphate buffer) $\lambda_{max}$ 297 nm (8,590). ir (Nujol mull) 1767 cm$^{-1}$ ($\beta$-lactam)

nmr (D$_2$O) $\delta$ 1.37 (d, J = 6Hz, CH$_3$—CH), 3.0–3.75

(m, —CH$_2$—), 4.2–4.8 (m, C$_{5H}$, C$_{6H}$, C$_{7H}$), 7.86

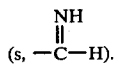

Following the procedure of Example 5, enhanced product isolation is achieved when the XAD-2 column is replaced by an otherwise equivalent column of Dowex 50-X4 (Na$^+$ cycle, 200–400 mesh).

EXAMPLE 6

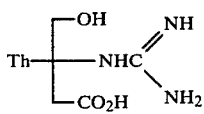

Preparation of N-Guanyl Thienamycin

Thienamycin (8.9 mg.) is dissolved in pH 7 0.1 N phosphate buffer (0.7 ml.) and N,N-dimethylformamide (0.3 ml.) and the solution brought to pH 9.5 by the addition of 2.5 N sodium hydroxide solution. To the magnetically solution is added O-methylisourea.hydrogen sulfate (43 mg.) causing a slight drop in pH. Additional sodium hydroxide solution is added to bring the pH back to 9.5 and the solution is stirred 30 minutes at 23° C. The solution is then acidified to pH 7.0. A sample of the solution containing a mixture of thienamycin and N-guanyl thienamycin shows two bioactive zones after electrophoresis (50 V/cm., 20 minutes, 0.05 N pH 7 phosphate buffer) and bioautography on S. aureus plates.

EXAMPLE 7

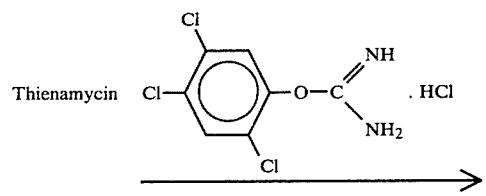

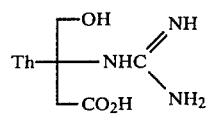

Preparation of N-Guanyl Thienamycin

Thienamycin (11 mg.) is dissolved in pH 7 0.1 N phosphate buffer (1 ml.) and adjusted to pH 8.3 with 0.1 N sodium hydroxide by means of an automatic dispensing burette. To the magnetically stirred solution is added O-2,4,5-trichlorophenylisourea.hydrochloride (76 mg.) portionwise to allow the auto burette to maintain a nearly constant pH. The reaction is run 4 hours at 22° C. and is then readjusted to pH 7.0 by the addition of dilute acid. A sample of this solution containing thienamycin and N-guanyl thienamycin is electrophoresed (50 V/cm., 25 minutes, pH 7 0.1 N phosphate buffer) and shows a positive Sakaguchi spray zone at 2.0 cm. towards the anode and a positive ninhydrin spray zone at 1.5 cm. in the same direction.

EXAMPLE 8

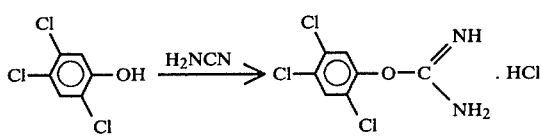

Preparation of O-2,4,5-Trichlorophenylisourea.Hydrochloride

A solution of cyanamide (0.28 mg.) in ether (0.50 ml.) is mixed with 2,4,5-trichlorophenol (12.5 g.); the mixture is heated to 70° C. and the melt magnetically stirred while the reaction flask is flushed with nitrogen. Dry hydrogen chloride gas is then slowly bubbled into the melt and the reaction is allowed to cool to 22° C. The resulting solid is washed thoroughly with ether and filtered to give O-2,4,5-trichlorophenylisourea.hydrochloride as a white solid, m.p. 205°–206° C.

EXAMPLE 9

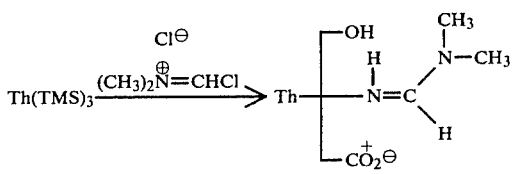

Preparation of N',N'-Dimethylaminomethylen Thienamycin

Thienamycin (16.5 mg.) is silylated with hexamethyldisilazane (200 μl.) and trimethylchlorosilane (60 μl.) in the usual manner. The silylated thienamycin is suspended in (ethanol free) chloroform (1 ml.) with magnetic stirring under a nitrogen atmosphere. The mixture is cooled to −45° C. and a solution of triethylamine (21 μl.) in chloroform (21 μl.) is added followed by a solution of (chloromethylene)-dimethylammonium chloride (11.5 mg.) in chloroform (50 μl.). The mixture is warmed to −25° C. over 1 hour and 0.1 N pH 7 phosphate buffer (5 ml.) is added. The mixture is vigorously stirred 15 minutes. The aqueous phase is separated and contains N-dimethylaminomethylene thienamycin which has an electrophoretic mobility (50 V/cm., 1 hour, pH 7 buffer) of 3.6 cm. towards the cathode.

EXAMPLE 10

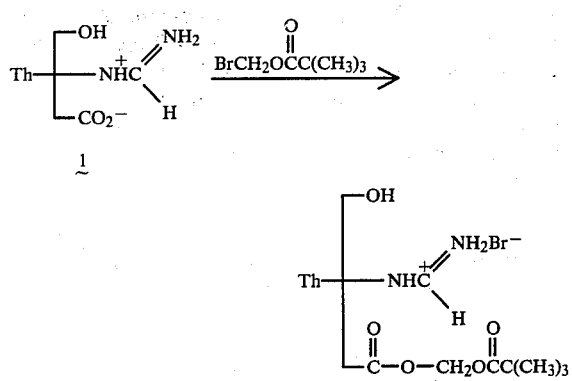

Preparation of N-Formimidoyl Thienamycin Pivaloxymethyl Ester Hydrobromide

N-aminomethylene thienamycin 1 (10 mg.) is dissolved in hexamethylphosphoramide (200 μl.) containing bromomethyl pivalate (10 μl.) and triethylamine (1 μl.) and magnetically stirred at 22° C. After 2 hours the hexamethylphosphoramide solution is dissolved in 2 ml. methylene chloride and the product precipitated with a 50% hexane-ether solution. The precipitate is dissolved in an aqueous 10% tetrahydrofuran solution and chromatographed on an XAD-2 resin packed column. N-Formimidoyl thienamycin pivaloxymethyl ester is isolated as a solid after tetrahydrofuran elution of the column and lyophilization.

EXAMPLE 11

Preparation of N-Trifluoroacetimidoyl Thienamycin

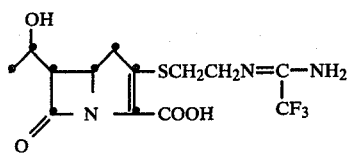

Thienamycin (199 mg) is dissolved in pH 7 0.1 N phosphate buffer (7 ml) and adjusted to pH 8.5 with 1 N sodium hydroxide solution. While maintaining this pH with an automatic burette, a solution of methyl trifluoroacetimidate (355 μl) in dioxane (2.5 ml) is added at once. After 30 minutes the pH is readjusted to 7.0 by the addition of 1 N hydrochloric acid. The solution is then chromatographed on Dowex 50-X4 resin (200 cc, Na+ cycle, 200–400 mesh) and is eluted with water. The N-trifluoroacetimidoyl Thienamycin derivative elutes in the first half column volume. This eluate is rechromatographed in a similar manner on Dowex 50-X4 (100 cc, Na+ cycle, 200–400 mesh) and the first column volume concentrated and chromatographed on XAD-2 resin (30 cc). The N-trifluoroacetimidoyl Thienamycin derivative elutes in 2.5–5.0 column volumes which is lyophilized to a white solid (15 mg). UV (pH 7 0.1 N phosphate buffer) λ$_{max}$ 302 nm (ε4,450). ir (Nujol mull) 1750 cm$^{-1}$ (β-lactam).

Electrophoresis: (50 v/cm, 20 min, pH 7, 0.1N phosphate buffer) mobility
2.0 cm (toward cathode)

EXAMPLE 12

Preparation of N-Acetimidoyl Thienamycin

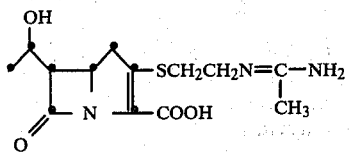

Thienamycin (190 mg) is dissolved in pH 7 0.1 N phosphate buffer (13 ml) and cooled in an ice bath with magnetic stirring. The solution is adjusted to pH 8.5 using 2.5 N sodium hydroxide solution dispensed from an automatic burette. While maintaining a pH of 8.5, ethyl acetimidate hydrochloride (400 mg) is added portionwise over a few minutes. After an additional 40 minutes the solution is adjusted to pH 7.0 with 2.5 N hydrochloric acid. The solution is then chromatographed on Dowex 50-X8 resin (250 cc, Na+ cycle, 100–200 mesh) and is eluted with water. The N-acetimidoyl derivative elutes in 1–2 column volumes (240–520 cc) and is lyophilized to a white solid (88 mg). UV (pH 7 0.1 N phosphate buffer) λ$_{max}$ 297 nm (ε7,620). ir (Nujol mull) 1774 cm$^{-1}$, β-lactam.

nmr (D$_2$O) δ 1.27 (d, J = 6 Hz, CH$_3$—CH) 2.24 (S, —C(=NH)—CH$_3$)
3.2–3.5 (m, —CH$_2$), 3.5–3.9 (m, —CH$_2$—)
4.2–4.6 (m; C$_{5H}$, C$_{6H}$, C$_{7H}$).

EXAMPLE 13

Preparation of N-[(4-pyridyl)(imino)methyl]thienamycin

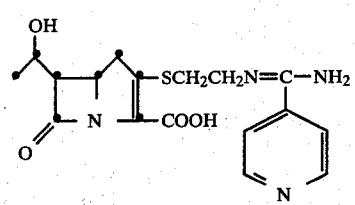

Thienamycin (80 mg., 0.294 mmole) is dissolved in aqueous sodium bicarbonate (24.7 mg., 0.294 mmole in 2.0 ml.) at 25° C. Methyl isonicotinimidate (80 mg., 0.588 mmole) is dissolved in the solution and progress of the reaction is followed by timed aliquots using high performance liquid chromatography (HPLC): Waters instrument; 0.2×61 cm. $C_{18}$ Bondapak reverse phase column; 1.5 ml/min aqueous 10% THF; UV (254 nm.) and R.I. monitors. The reaction is essentially complete in 40 minutes, and the reaction solution is chromatographed directly over an 18.4×270 mm. XAD resin column, first eluting with deionised, distilled water, then changing to aqueous 10% THF. The eluate is monitored by UV and HPLC is used to locate the pure product. Correct fractions are combined and lyophilized to yield a colorless, fluffy powder (80 mg. 73%). UV $\lambda_{max}^{H2O}$ 298 nm ($\epsilon$7,800); IR (Nujol mull) 1762 cm$^{-1}$ ($\beta$-lactam); NMR (60 MHz, $D_2O$), $\delta$1.27, 3H (d, J=7 Hz, $\underline{CH_3}$.CH(OH); $\delta$7.75 and 8.80, 4H, (m, m, 4-pyridyl); HPLC, 1.58×retention of thienamycin, conditions as above.

EXAMPLE 14

Following the procedure of Example 13, but replacing the reagent with methyl picolinimidate, there is obtained: N-[(2-pyridyl)(imino)methyl]thienamycin (85 mg 77%) UV $\lambda_{max}^{H2O}$ 267, 300 nm ($\epsilon$, 8,150, 7,600); IR (Nujol mull) 1764 cm$^{-1}$ ($\beta$-lactam); NMR (60 MHz, $D_2O$), $\delta$1.24, 3H (d, J=7 Hz, $\underline{CH_3}$.CH(OH)); $\delta$7.80, 8.07, 8.80, 4H, (m,m,m, 2-pyridyl); HPLC, 1.8×retention of thienamycin.

EXAMPLE 15

Following the procedure of Example 13, but replacing the reagent with methyl nicotinimidate, there is obtained: N-[(3-pyridyl(imino)methyl]thienamycin (77 mg., 70%): UV $\lambda_{max}^{H2O}$ 264, 299 nm, ($\epsilon$5570, 6120); IR, (Nujol mull), 1766 cm$^{-1}$ ($\beta$-lactam); NMR, (60 MHz, $D_2O$), $\delta$1.24, 3H, (d, J=7 Hz, $\underline{CH_3}$.CH(OH)); $\delta$7.6, 8.2, 8.9, 4H, (m,m,m, 3-pyridyl); HPLC, 1.57×retention of thienamycin.

EXAMPLE 16

Following the procedure of Example 13, but replacing the reagent with methyl 4-thiazolecarboximidate, there is obtained: N-[(4-thiazolyl)(imino)methyl]thienamycin (99 mg, 89%): UV $\lambda_{max}^{H2O}$ 300 nm, ($\epsilon$7530); IR (Nujol Mull) 1764 cm$^{-1}$ ($\beta$-lactam); NMR (60 MHz, $D_2O$), $\delta$1.23, 3H, (d, J=7 Hz, $\underline{CH_3}$.CH(OH)); $\delta$8.60, 9.17, 2H (d,d, J=2 Hz, 4-thiazolyl); HPLC, 1.8×retention time of thienamycin.

EXAMPLE 17

Preparation of N-Allylformamide

A mixture of allylamine (5.00 g., 87.6 mmole) and methylformate (5.26 g., 87.6 mmole) is stirred at 25° C., for 2 hours. At the end of this time, the reaction flask is fitted with a short path distillation head and the desired N-allylformamide is collected at 89°–90° C./0.7 mm as a colorless oil. Yield 7.0 g. (94%). IR(CHCl$_3$) 3380, 1680 cm$^{-1}$; nmr (CHCl$_3$) $\delta$8.1 (1H, br s), $\delta$6.4–7.9 (1H, very br), $\delta$5.5–6.3 (1H, m), $\delta$4.9–5.5 (2H,m), $\delta$3.85 (2H, m).

EXAMPLE 18

Preparation of Ethyl Allylimidate Hydrochloride

Ethyl chloroformate (2.66 g., 24.47 mmole) is added by syringe to N-allylformamide (2.08 g., 24.47 mmole) in a dry flask under $N_2$. The resulting mixture is then stirred at 25° C., for 2 hours during which time $CO_2$ is rapidly evolved. The reaction mixture is then heated to 45° C. until no further evolution of gas is evident (2 hours). The viscous product is then cooled and held at a vacuum of 0.2 mm for 2 hours to remove all volatiles.

EXAMPLE 19

Preparation of N'(2-Methylthioethyl)N-Formimidoyl Thienamycin

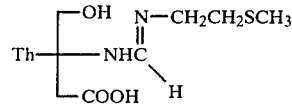

Thienamycin (105 mg.) is dissolved in pH 7 0.1 N phosphate buffer (5 ml.) and to this is added a solution of ethyl N-2-methylthioethyl formimidate (300 $\mu$l) in tetrahydrofuran (2 ml.). The pH of the solution is adjusted to and maintained at 8.5 using an autoburette dispensing 1 N NaOH. After 30 minutes the pH is adjusted to 7.0 with 2.5 N HCl. The solution is chromatographed on an ice water jacketed column of Dowex 50-X4 resin (53 cc, Na$^+$ cycle, 200–400 mesh) eluted with deionized water. The N'[2-methylthioethyl]N-formimidoyl derivative elutes in 2–4 column volumes and is lyophilized to give a white solid. U.V. (pH 7 0.1 N phosphate buffer) $\lambda$max 298 nm ($\epsilon$7,760) i.r. (Nujol mull) 1760 cm$^{-1}$ ($\beta$-lactam).

EXAMPLE 20

Preparation of N'-Tert-Butyl-N-Formimidoyl Thienamycin

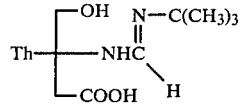

Thienamycin (105 mg.) is dissolved in pH 7 0.1 N phosphate buffer (5 ml.) and to this is added a solution of ethyl N-tert-butyl formimidate (290 mg.) in tetrahydrofuran (1 ml.). The pH of the solution is adjusted to and maintained at 8.5 using an autoburette dispensing 1 N NaOH. After 30 minutes, the pH is adjusted to 7.0 with 2.5 N HCl. The solution is chromatographed on an ice water jacketed column of Dowex 50-X4 resin (53 cc, Na$^+$ cycle, 200–400 mesh) eluted with deionized water. The fractions containing the title product are combined and lyophilized.

EXAMPLE 21

Preparation of N'[1-Methyl-2-Propenyl]N-Formimidoyl Thienamycin

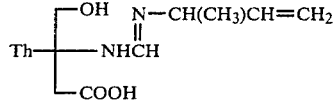

Thienamycin (126 mg.) is dissolved in pH 7 0.1 N phosphate buffer (6 ml.) and the pH of the solution is adjusted to 8.5 using an automatic burette dispensing 1 N NaOH. To this stirred solution is added ethyl N-1-methyl-2-propenyl-formimidate hydrochloride (300 $\mu$l) while the pH is maintained at 8.5. After 30 minutes, the pH of the solution is adjusted to 7.0 with 2.5 N HCl and the solution is chromatographed on a ice water jacketed column of Dowex 50-X4 resin (49 cc, Na+ cycle 200-400 mesh) eluted with deionized water. The N'[1-methyl-2-propenyl]N-formimidoyl derivative elutes in 2-4 column volumes and is lyophilized to a white solid (59 mg.). U.V. (pH 7 0.1 N phosphate buffer) i.r. (Nujol mull) 1760 cm$^{-1}$ (β-lactam); UV: λmax.=2.99 nm (absorptivity (ε)=7,820).

EXAMPLE 22

Preparation of N-(1-Buten-3-yl)Formamide

A solution of 3.5 g. (0.05 mole) 3-amino-1-butene in 12 ml. of methylformate is kept at 25° C. for 20 hours; the solution is then concentrated under reduced pressure to remove excess methylformate. The residual N-(1-buten-3-yl)formamide is distilled under reduced pressure. A fraction amounting to 3 g. (b.p. 58°-60° C./0.5 mm) of N-(1-buten-3-yl)formamide is obtained.

EXAMPLE 23

Preparation of Ethyl-N-(1-Buten-3-yl)Formimidate

A mixture of 1.0 g. of N-(1-buten-3-yl)formamide and one equivalent of ethylchloroformate is stirred under $N_2$ for 4 hours during which time $CO_2$ is evolved. The solution is stirred under reduced pressure for 3 hours to remove any unreacted ethylchloroformate, and a residue of ethyl-N-(1-buten-3-yl)formimidate is obtained.

EXAMPLE 24

Preparation of Methyl N-Dimethylaminoformimidate

To a stirred solution of N,N-dimethylformhydrazide (0.22 g) in 2.0 ml of chloroform, under nitrogen, is added methylchloroformate (0.5 ml). The mixture is heated at 40° C. for three hours then evaporated under nitrogen. The mixture is triturated with anhydrous ether. The supernatant solution is decanted and the residue dried in a stream of nitrogen. Yield: 284 mg. nmr $CDCl_3\delta$, 9.13(CH); 3.80($OCH_3$), 3.01(N($CH_3$)$_2$).

EXAMPLE 25

Preparation of Cyclopropyl Formamide

A mixture of cyclopropylamine (5.00 g, 87.6 mmole) and methylformate (5.26 g, 87.6 mmole) is stirred at 25° C., for 2 hours. (an initial exotherm is noted). The mixture is then placed on the rotary evaporator to remove the MeOH formed in the reaction. The remaining material is distilled through a short path head to yield 6.92 g (93%) of the desired N-cyclopropyl formamide as a colorless oil, n.m.r. ($CDCl_3$) δ8.1 (1H, br S), 6.8-8.5 (1H, br), δ2.4-3.0 (1H, m), δ0.4-1.0 (4H,m).

EXAMPLE 26

Preparation of Ethyl N-Cyclopropyl Formimidate

Ethylchloroformate (4.078 g, 37.58 mmole) is added by syringe to N-cyclopropylformamide (3.194 g, 37.58 mmole) in a dry flask under $N_2$. After an induction period of 30 sec., a rapid evolution of gas begins. The resulting reaction mixture is stirred at 25° C. until no further evolution of gas can be detected (~4 hr), then the viscous product is subjected to a vacuum of 0.5 mm for 1 hr to remove any unreacted ethyl chloroformate. NMR analysis of the product shows the formyl proton at δ9.37 as a broad singlet. ($CDCl_3$ solution).

EXAMPLE 27

Preparation of Ethyl N(Methylthioethyl)formimidate

To a 60 ml separatory funnel are added ethyl formimidate hydrochloride (0.97 g, 8.8 mmole) a solution of β-methylthioethylamine (0.80 g, 8.8 mmole) in $CH_2Cl_2$ (35 ml), and $H_2O$ (35 ml.). The mixture is shaken vigorously for 5 minutes. The $CH_2Cl_2$ layer is separated, washed with brine, dried with $MgSO_4$, filtered, and evaporated under reduced pressure to give the crude imidate (0.59 g) as a hazy, pale, yellow liquid. i.r. 1600, 1230 cm$^{-1}$.

EXAMPLE 28

Preparation of N'-Dimethylamino-N-Formimidoyl Thienamycin

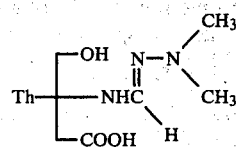

Thienamycin (115 mg.) is dissolved in pH 7 0.1 N phosphate buffer (7 ml.) and the pH of the soluton is adjusted to 8.5 using an automatic burette dispensing 1 N NaOH. To this stirred solution is added methyl N-dimethylamino formimidate hydrochloride (284 mg.) while the pH is maintained at 8.5. After 20 minutes the pH of the solution is adjusted to 7.0 using 2.5 N HCl and the solution is chromatographed on Dowex 50-X4 resin (53 cc, Na+ cycle, 200-400 mesh) eluted with deionized water. The chromatography is carried out in a water jacketed column at 3°. The N'-dimethylamino-N-formimidoyl derivative elutes in 2 column volumes and is lyophilized to a white solid (40 mg.) UV (pH 7, 0.1 N phosphate buffer) λmax 298 nm (ε6, 910) ir (Nujol mull) 1760 cm$^{-1}$ (β-lactam) nmr ($D_2O$) ε1.29 (d, J=6 Hz, $CH_3$-CH), 2.59 (s, N($CH_3$)$_2$), 7.76 (s, NCH).

EXAMPLE 29

Preparation of Methyl Oxalimidoyl Thienamycin

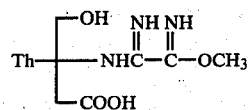

Thienamycin (105 mg.) is dissolved in pH 7 0.1 N phosphate buffer (5 ml.) and the pH of the solution is adjusted to 8.5 using an automatic burette dispensing 1 N NaOH. To this solution is added methyl oxalimidate (200 μl) while the pH is maintained at 8.5. After 30 minutes the pH is adjusted to 7.0 using 2.5 N HCl and the solution is chromatographed on Dowex 50-X4 resin (53 cc, Na+ cycle, 200-400 mesh) eluted with deionized water. The chromatography is carried out in water jacketed column at 3°. The methyl oxalimidoyl derivative elutes in 2 column volumes and is lyophilized to a white solid (44 mg.) uv (pH 7 0.1 N phosphate buffer) λmax 298 nm (ε6, 230) ir (Nujol mull) 1760 cm$^{-1}$ (β-lactam); nmr ($D_2O$) δ1.27 (d, J=6 Hz, $CH_3$—CH), 3.87 (s, —$OCH_3$).

EXAMPLE 30

Preparation of N-Propionimidoyl Thienamycin

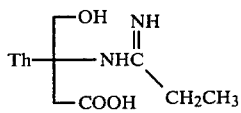

Thienamycin (114 mg.) id dissolved in pH 7 0.1 N phosphate buffer (10 ml.) and the pH of the solution is adjusted to 8.5 using an automatic burette dispensing 1 N NaOH. Solid ethyl propionimidate hydrochloride (231 mg.) is added portionwise as rapidly as possible allowing the pH to be maintained near 8.5. After 30 minutes the pH is adjusted to 7.0 using 2.5 N HCl and the solution is chromatographed on Dowex 50-X4 resin (72 cc, Na+ cycle, 200-400 mesh) eluted with deionized water. The N-propionimidoyl derivative elutes in 2 column volumes and is lyophilized to a white solid (76 mg.). uv (pH 7 0.1 N phosphate buffer) λmax 298 nm (ε7,830) nmr (D$_2$O) δ1.28 (d, J=6 Hz, $\underline{CH_3}$ CH(OH)), 1.23 (t, J=8 Hz, —CH$_2$—$\underline{CH_3}$), 2.50 (q, J=8 Hz, $\underline{CH_2}$CH$_3$).

EXAMPLE 31

Preparation of N'-Methyl-N-Formimidoyl Thienamycin

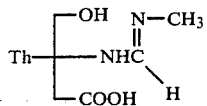

Thienamycin (140 mg.) is dissolved in pH 7 0.1 N phosphate buffer (10 ml.) and the pH of the solution is adjusted to 8.5 using an automatic burette dispensing 1 N NaOH. To this solution is added methyl N-methyl formimidate hydrochloride (200 μl) while the pH is maintained at 8.5. After 40 minutes the pH is adjusted to 7.0 using 2.5 N HCl and the solution is chromatographed on Dowex 50-X4 resin (72 cc, Na+ cycle, 200-400 mesh) eluted with deionized water. The N'-methyl-N-formimidoyl derivative elutes in 2 column volumes and is lyophilized to a white solid (43 mg.). uv (pH 7 0.1 N phosphate buffer) λmax 298 nm (ε7,250) ir (Nujol mull) 1765 cm$^{-1}$ (β-lactam). nmr (D$_2$O) δ1.29 (d, J=6 Hz, $\underline{CH_3}$—CH), 2.92 (s, N—CH$_3$) 7.80 (s, N—CH).

EXAMPLE 32

Preparation of N'-Benzyl-N-Formimidoyl Thienamycin

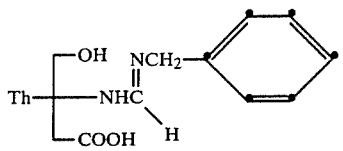

Thienamycin (110 mg.) is dissolved in pH 7 0.1 N phosphate buffer (7 ml.) and the pH of the solution is adjusted to 8.5 using an automatic burette dispensing 1 N NaOH. A solution of ethyl N-benzyl formimidate fluroborate (572 mg.) in p-dioxane (2 ml.) is added to the buffered solution while the pH is maintained at 8.5. After 20 minutes the pH of the solution is adjusted to 7.0 using 2.5 N HCl and chromatographed on Dowex 50-X4 resin (53 cc, Na+ cycle, 200-400 mesh) eluted with deionized water. The chromatography is carried out in a water jacketed column at 3°. The N'-benzyl-N-formimidoyl derivative elutes in 2 column volumes and is lyophilized to a white solid (5 mg.). uv (pH 7 0.1 N phosphate buffer) λmax 295 nm (ε3,980) ir (Nujol mull) 1765 cm$^{-1}$ (β-lactam) nmr (D$_2$O) δ1.29 (d, J=6 Hz, $\underline{CH_3}$CH), 4.44 (s, $\underline{CH_2}$-Ar), 7.37 (s, Aryl), 8.14 (s, NCH).

EXAMPLE 33

Preparation of N'-Isopropyl-N-Formimidoyl Thienamycin

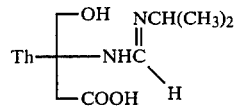

Thienamycin (110 mg.) is dissolved in pH 7 0.1 N phosphate buffer (7 ml.) and the Ph of the solution is adjusted to 8.5 using an automatic burette dispensing 1 N NaOH. A solution of methyl N-isopropyl formimidate hydrochloride (300 mg.) in p-dioxane (1 ml.) is added to the magnetically stirred buffered solution while the pH is maintained at 8.5. After 25 minutes the pH of the solution is adjusted to 7.0 using 2.5 N NaOH and chromatographed on Dowex 50-X4 resin (53 cc, Na+ cycle, 200-400 mesh) eluted with deionized water. The chromatography is carried out in a water jacketed column at 3° C. The N'-isopropyl-N-formimidoyl derivative elutes in 2 column volumes and is lyophilized to a white solid (12 mg.). UV (pH 7 0.1 N phosphate buffer) λmax 299 nm (ε8,130) ir (Nujol mull) 1760 cm$^{-1}$ (β-lactam) nmr (D$_2$O) δ1.26 (d, J=6 Hz, $\underline{CH_3}$CH(OH)), 1.29 (d, J=6 Hz, CH($\underline{CH_3}$)$_3$), 7.89 (s, NHCH), 7.96 (s, NHCH).

EXAMPLE 34

Preparation of N(N'-Allyl-Formimidoyl)Thienamycin

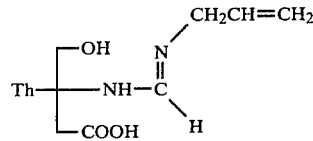

To a prechilled sample of Thienamycin (123 mg., 0.452 mmols) is added 13 ml. of cold 0.1 N phosphate buffer. The solution is adjusted to pH 9 with 1.0 N sodium hydroxide. To this basic solution at 2° C. is added all at once ethyl N-allyl-formimidate hydrochloride (0.3 g.). The pH dropped to 7.3 and is brought back to 8.5 with additional sodium hydroxide. The reaction mixture is stirred at 2° C. for an additional 30 min. and the pH is adjusted to 7 with cold 0.1 N sulfuric acid. The reaction mixture is assayed using high pressure liquid chromatography on a C$_{18}$-Porosil column, developed with 10% aqueous tetrahydrofuran and is found to show only trace amounts of Thienamycin (retention time, 5 min.) and substantially pure product (retention time, 10.5 min.). The reaction mixture is chromatographed on a Dowex-50×4 column (60 ml., Na cycle 200-400 mesh) eluting with water at a flow rate of 0.5 ml/min/cm² of resin bed. After discarding the first 400 ml. of eluate, the next 150 ml. is lyophilized to give the product. Yield γ96 mg. (63%). U.V. λmax 301 nm, 24.6 O.D.U./mg. (NH₂OH extinguished) 90% purity. IR Nujol exhibits C=O at 5.67μ and 5.90μ. NMR 100 MHz D₂O shows its a 1:1 mixture of syn- and anti-N(N'-allyl-formimidoyl)Thienamycin.

EXAMPLE 35

Preparation of N(N'-Trifluoroethyl-Formimidoyl)Thienamycin

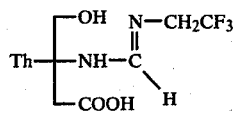

To a prechilled sample of Thienamycin (123 mg., 0.452 mmoles) is added 15 ml. of cold 0.1 N phosphate buffer. The solution is adjusted to pH 9 with 1 N sodium hydroxide. To this basic solution at 0°–2° C. is added ethyl N-trifluroethyl-formimidate (0.3 ml.) in dioxane (2 ml.) portionwise over 30 min. The pH of the reaction is maintained at 8.5–9 during the addition. The reaction mixture is stirred for a few minutes. After the addition of imidate is completed and the pH is brought to 7 with cold 0.1 N H₂SO₄.HPLC, C₁₈ Porosil reverse phase, using 10% aqueous-tetrahydrofuran exhibits a new peak at 12.2 min. assayed to the desired product. The mixture is chromatographed on a Dowex 50×4 column (60 ml. 200–400 mesh). The column is eluted with water at a flow rate of 0.5 ml/min/cm² of resin bed. The forerun is discarded and fractions containing the product are combined and lyophilized to give a hygroscopic solid, 10.2 mg. λmax 302 nm.

EXAMPLE 36

Preparation of N(N'-Carboxymethyl-Formimidoyl)Thienamycin Sodium Salt

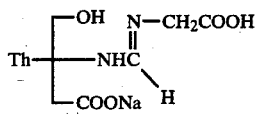

Thienamycin (130 mg.) is dissolved in pH 7 0.1 N phosphate buffer (4 ml.) and solid sodium ethyl N-carboxymethyl formimidate (500 mg.) is added at once. The pH of the solution is adjusted to 8.5 using an automatic burette dispensing 1 N NaOH. After 25 min. at pH 8.5 the solution is adjusted to 7.0 with 2.5 N HCl. The solution is then chromatographed on an ice-water jacketed column of Dowex 50-x4 resin (51cc, Na⁺ cycle, 200–400 mesh) eluted with deionized water. The eluate of the first column volume was combined and concentrated to 7 ml. This solution was then chromatographed on an ice-water jacketed column of XAD-2 resin (53 cc) eluted with deionized water. The second through fourth column volumes were collected and combined and lyophilized to give sodium N,(N'-carboxymethylformimidoyl)Thienamycin (25 mg). uv (pH 7 0.1 N phosphate buffer) λmax 300 nm (ε6,390) ir (Nujol mull) 1755 cm⁻¹ (β-lactam) nmr (D₂O) δ1.29 (d, J=6 Hz, CH₃CH), 7.85 (s, NCH).

EXAMPLE 37

Preparation of N(3-azidopropionimidoyl)Thienamycin

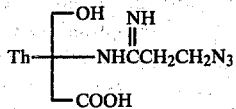

To a solution of Thienamycin (133 mg.) in 10 ml. 0.1 M pH 7.0 phosphate buffer is added 1.2 g. of O-ethyl-3-azidopropionimimidate.HCl while the solution is maintained at pH 8.5 with 2.5 N NaOH. The mixture is stirred at 0° C. for 0.5 hr., then is neutralized with 2.5 N HCl to pH 7.0, concentrated to 5 ml. and chromatographed on a Dowex 50W x 8 (Na form) column (1.5"×12") which is eluted with water to give 30 mg. of the desired product. The product shows UV $\lambda_{max}H_2O$ 300 nm; high pressure liquid chromatography (HPLC) retention time of 10 min. with comparison to that of 4.8 min. of the starting material under the same conditions (⅛"×2', Bondapak C₁₈ reverse phase column eluted with 10% THF in water at flow rate of 1.5 ml./min.); Electrophoretic mobility 5 mm toward cathode at 50 V/CM for 20 min. in 0.05 M pH 7.0 phosphate buffer.

EXAMPLE 38

Preparation of N(3-aminopropionimidoyl)thienamycin

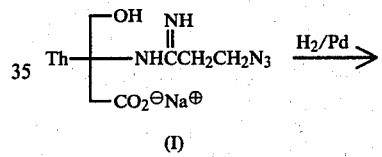

(I)

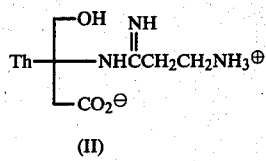

(II)

N-(3-azidopropionimidozyl)tienamycin (I) (43 mg in 40 ml water) is hydrogenated under 1 atm of H₂ in the presence of 0.1 g Pd catalyst (10% Palladium on charcoal) for 30 min. Electrophoresis of the resulting mixture shows a new bio-active product which moves 30 mm toward cathode (50 V/cm for 20 min in 0.05 M pH 7.0 phosphate buffer) in addition to the starting material (I) which moves 5 mm toward cathode. The electrophoretic mobility of the product is consistent with that of the expected product (II). The resulting reaction mixture from the hydrogenation reaction is neutralized with 2.5 N HCl and filtered from the catalyst. The filtrate is concentrated to 10 ml and chromatographed on XAD-2 resin (2.3×16 cm column). The column is eluted with water to provide the desired product II as the hydrochloride after lyophilization (23 mg; N-3-aminopropionimidoyl)thienamycin hydrochloride); U.V. absorbance maxium in water=301 nm (absorptivity=7080); I.R.: nujol mull 1765 cm⁻¹; nmr: 60 mHz, D₂O δ1.30 ppm (doublet, 3), δ2.60–3.72 ppm (multiplet, 11), δ4.18 ppm (multiplet 2).

EXAMPLE 39

Preparation of N-Nitroguanyl Thienamycin

Thienamycin (131 mg) is dissolved in a solution of dimethyl sulfoxide (10 ml), tri-n-butylamine (0.30 ml), and 2-methyl-1-nitro-2-thiopseudourea (0.3 g). The solution is heated in a water bath at 45° C. while a stream of nitrogen is vigorously bubbled into the solution. After 50 min. the solution is concentrated under high vacuum to 1.0 ml. and dissolved in 0.05 N pH7 phosphate buffer (7 ml). The unreacted thiopseudourea is precipitated and removed by filtration. The solution is then chromatographed on Dowex 50-X4 resin (53 cm$^3$, 200–400 mesh, Na$^+$ cycle) and eluted with water. The N-nitroguanyl derivative elutes in the first column volume and is lyophilized to a solid (23%). UV (pH7 0.1 N phosphate buffer) $\lambda_{max}$ 269 nm ($\epsilon$11,000) Electrophoresis (40 v/cm, pH7 0.1 N phosphate buffer, 20 min) 3.0 cm toward cathode.

EXAMPLE 40

Preparation of the N-Isobutyrimidoyl Thienamycin

Following the procedure of Example 12 but replacing ethyl acetimidate hydrochloride with isobutyrimidate hydrochloride and allowing the reaction to proceed at 20° C. and pH 8.2 there is obtained N-isobutyrimidoyl thienamycin (14%). UV (pH7 0.1 N phosphate buffer) $\lambda_{max}$ 298 nm ($\epsilon$8,290) NMR (D$_2$O $\delta$ 1.27 (d, J=7 H$_z$, CH(CH$_3$)$_2$, 1.29 (d, J=6 H$_z$, C$\underline{H}_3$CH(OH), 2.79 (heptet, J=7 H$_z$, C$\underline{H}$(CH$_3$)$_2$).

EXAMPLE 41

Preparation of N'-Methyl-N-Acetimidoyl Thienamycin

Following the procedure of Example 12, but replacing ethyl acetimidate hydrochloride with Methyl-N-methyl acetimidate, there is obtained N-methyl-N'-acetimidoyl thienamycin (10%). UV (ph7 0.1 N phosphate buffer) $\lambda_{max}$ 298 nm ($\epsilon$6,700) IR (Nujol mull) 1750 cm$^{-1}$ ($\beta$-lactam), 1660 cm$^{-1}$ (C=NCH$_3$)

NMR (D$_2$O)$\delta$ 1.27 (d, J = 6H$_z$, CH$_3$CH(OH), 2.22 and 2.25 (S, N—$\overset{\overset{\text{N}}{\|}}{\text{C}}$CH$_3$), 2.97 (S, NCH$_3$)

EXAMPLE 42

Preparation of N'-Methyl-N-Formimidoyl Thienamycin

Following the procedure of Example 12, but replacing ethyl acetimidate hydrochloride with ethyl N-methyl formimidate hydrochloride there is obtained N'-methyl-N-formimidoyl thienamycin (10%). UV (pH7 0.1 N phosphate buffer) $\lambda_{max}$ 298 nm NMR (D$_2$O)$\delta$ 1.30 (d, J = 6H$_z$, CH$_3$CH(OH), 2.92 (S, N—CH$_3$), 7.78 (S, $\overset{\overset{\text{N}}{\|}}{-}$CH)

EXAMPLE 43

Following the procedure of Example 12, but replacing the reagent with an equivalent amount of methyl methoxyacetimidate, there is obtained: N(methoxyacetimidoyl)thienamycin (34%); UV $\lambda_{max}$H$_2$O 198, 301 nm ($\epsilon$16,180, 8,700); IR (Nujol mull) 1760 cm$^{-1}$ ($\beta$-lactam); NMR (60 MHz, D$_2$O) $\delta$1.28, 3H, (d, J=6 Hz, C$\underline{H}_3$.CH(OH); $\delta$3.50, 3H, (S, C$\underline{H}_3$.O.CH$_2$) $\delta$4.35, 2H, (S, CH$_3$.O.C$\underline{H}_2$); HPLC, 1.50×retention time of thienamycin.

EXAMPLE 44

Preparation of Ethyl N-Methoxyformimidate

A mixture of methoxyamine hydrochloride (0.020 mole, 1.6700 g) and anhydrous potassium carbonate (0.010 mole, 1.3821 g) is dissolved in 7.0 ml water. Ether 80 ml is added and the reaction mixture is treated with ethyl formimidate hydrochloride (0.02 mole, 2.1900 g). The mixture is shaken for 15 minutes. The ether layer is separated and the aqueous layer is extracted with two portions of ether (30 ml). The combined and dried ether solution is evaporated to give 0.8433 g of ethyl N-methoxyformimidate.

nmr
$\delta$1.36 (triplet)
$\delta$3.83 (singlet)
$\delta$4.13 (quartet)
$\delta$6.56 (singlet)

EXAMPLE 45

Ethyl N-(2,2,2-trifluoroethyl)formimidate

Ethyl formimidate hydrochloride (0.555 g, 5 mmole), 2,2,2-trifluoroethylamine hydrochloride (0.677 g, 5 mmole) and potassium carbonate (0.345 g, 2.5 mmole) are suspended in 20 ml CH$_2$Cl$_2$ and treated with 2 ml H$_2$O. The mixture is shaken vigorously for 3 minutes. The organic phase is separated and the aqueous extracted twice with 10 ml portions of CH$_2$Cl$_2$ The combined organic phase is dried and the CH$_2$Cl$_2$ distilled through a Vigreauxe column to give the Ethyl N-(2,2,2-trifluoroethyl)formimidate. n.m.r. $\delta$1.33 t (CH$_3$CH$_2$); 3.8 q (j=10 c.p.s., CF$_3$ CH$_2$) 4.23 q (j=7.5, CH$_3$CH$_2$O); 7.6 S (H—C=N).

EXAMPLE 46

Preparation of Ethyl N-ethoxycarbonylethyl-formimidate

Ethyl formimidate hydrochloride (0.55 g, 5 mmole) ethyl glycinate hydrochloride (0.697 g, 5 mmole) and potassium carbonate (0.345 g, 2.5 mmole) are suspended in 20 ml CH$_2$Cl$_2$ and treated with 2 ml H$_2$O. The mixture is shaken vigorously for 4 minutes. The organic phase is separated, the aqueous phase is extracted twice with CH$_2$Cl$_2$ (10 ml) and the combined organic phase is dried and evaporated to give Ethyl N-ethoxycarbonyl-methyl-formimidate. n.m.r. $\delta$: 1.26 t (CH$_2$—CH$_2$); 4.06 S (N—CH$_2$—C); 4.23 q (CH$_3$CH$_2$—O); 7.5 S (N=CH).

EXAMPLE 47

Preparation of Potassium N-ethoxycarbonylmethyl-formimidate

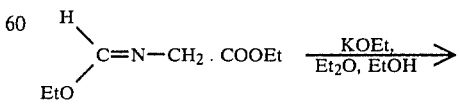

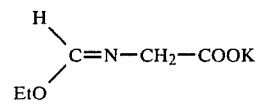

Potassium (0.18 g) is dissolved in a mixture of 0.6 g EtOH and 4 ml Et$_2$O under N$_2$. The solution is diluted with 50 ml of Et$_2$O and ethyl N-ethoxycarbonylmethyl-formimidate (0.79 g) in 2 ml Et$_2$O is added, followed by 0.1 ml H$_2$O. Rapid crystallization of the salt takes place. The solid is filtered, washed with ether and dried under vacuum to give Potassium N-ethoxycarbonylmethyl-formimidate. n.m.r. (D$_2$O) 1.13 t (CH$_3$CH$_2$); 3.63 g (CH$_3$—CH$_2$O); 3.8 S (N—CH$_2$—C); 8.06 S N=CH.

EXAMPLE 48

Preparation of Ethyl N-Benzylformimidate

A solution of 690 mg (5.1 mmoles) of N-benzylforma-mide in 5 ml of methylene chloride is cooled in an ice-water bath and put under an argon blanket. The solution is stirred while 4.9 ml (4.9 mmoles) of 1 M triethylox-onium fluoroborate in methylene chloride is added dropwise. After a 45 minute reaction time, the mixture is concentrated to dryness under reduced pressure at room temperature, and the residue is dried under reduced pressure over P$_2$O$_5$. The nuclear magnetic resonance spectrum of the product in deuterochloroform is fully in accord with the product being a fluoroborate etherate complex of ethyl N-benzylformimidate.

EXAMPLE 49

Preparation of N-isopropyl formamide

Formamide (1.13 g, 0.98 ml) is dissolved in 10 ml of toluene, containing toluenesulfonic acid (4.7 g). To the above mixture is added isopropylamine (2.95 g,, 4.25 ml). The mixture is refluxed overnight under a gentle stream of N$_2$. The solution is filtered and the toluene is evaporated under reduced pressure. The residual oil is distilled at 59°–62° C./.07 mm to give 1.0 g of the desired product.

EXAMPLE 50

Preparation of Methyl N-isopropyl formimidate

Isopropyl formamide (535 mg) is treated with an equivalent amount of ethyl chloroformate (440 μl) for 2–3 hours under N$_2$ at 40°–45° C. The mixture is washed successively with petroleum ether anhydrous ether and benzene leaving the product as an oil.

EXAMPLE 51

Preparation of N-[N'-ethylformimidoyl]thienamycin

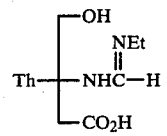

Thienamycin (100 mg) in 10 ml 0.1 M pH 7.0 phosphate buffer is adjusted and maintained at pH 8.5–9.0 with 2.5 N sodium hydroxide. To the solution is added 300 mg. of ethyl N-ethylformimidate hydrochloride. The mixture is stirred at 23° C. for 20 minutes, then is neutralized to pH 7.0 with 2.5 N HCl and chromatographed on a Dowex—50×8 (Na form) ion-exchange column (1.5"×10"). The column is eluted with water taking 6.7 ml fractions. Fractions 40–90 are combined, concentrated and freeze-dried to give 15 mg of the solid product. Electrophoresis of the product at 50 V/cm for 20 minutes in 0.1 M, pH 7.0 phosphate buffer shows a single bioactive zone which moves 2 mm toward the cathode. uvλ$_{max}$H$_2$O 301 nm; nmr (100 MH$_2$, D$_2$O); δ7.77 (S) and 7.82 (S) (formimidoyl CH).

EXAMPLE 52

Preparation of N-[N'-cyclopropylformimidoyl]thienamycin

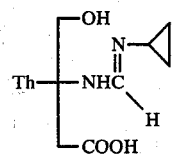

Thienamycin (100 mg) in 10 ml 0.1 M, pH 7.0 phosphate buffer is adjusted and maintained at pH 8.5–9.0 while 300 mg of ethyl N-cyclopropylformimidate hydrochloride is added dropwise to the solution. The mixture is stirred at 23° for 40 minutes, then is neutralized, and chromatographed on a Dowex—50×8 (Na form) ion-exchange column (1.5"×10"). The column is eluted with water, collecting 6.5 ml fractions. Fractions 43–95 are combined, concentrated and freeze-dried to give 54 mg of the solid product. Electrophoresis of the product shows a single bio-active zone which moves 10 mm toward the cathode (50 V/CM, 1 hour in 0.05 M pH 7.0 phosphate buffer). uvλ$_{max}$H$_2$O 301 nm; Nmr (100 MHz, D$_2$O): 0.60–1.30 ppm (m, cyclopropyl) and 7.80 ppm (formimidoyl CH).

EXAMPLE 53

Following the procedure set forth in the foregoing text and examples, the following compounds of the present invention are obtained. The reagents, imido ethers and imido halides, utilized in the reaction with thienamycin, or a derivative thereof, to provide the following compounds are either known, or may be prepared as described above.

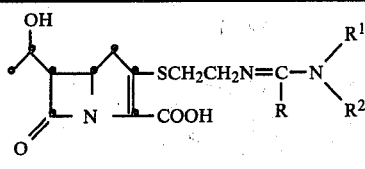

| Compound | R | R$^1$ | R$^2$ |
|---|---|---|---|
| 1. | H | —CH$_2$CH$_2$CH$_2$CH$_3$ | H |
| 2. | H | —CH$_2$—CH(CH$_3$)—CH$_3$ | H |

-continued

| | | | |
|---|---|---|---|
| 3. | H | —CH(CH₃)CH₂CH₃ | H |
| 4. | H | —CH₂CH₂CH₂CH₂CH₃ | H |
| 5. | H | —CH(CH₃)—CH₂CH₂CH₃ | H |
| 6. | H | —CH₂CH(CH₃)—CH₂CH₃ | H |
| 7. | H | —CH(CH₃)—CH(CH₃)—CH₃ | H |
| 8. | H | —C(CH₃)₂—CH₂—CH₃ | H |
| 9. | H | —CH₂—C(CH₃)₃ | H |
| 10. | H | —CH₂CH₂CH₂CH₂CHCH₃ | H |
| 11. | H | —CH(CH₃)—CH₂CH(CH₃)₂ | H |
| 12. | H | —CH₂—C(CH₃)=CH₂ | H |
| 13. | H | —CH₂—CH=CH—CH₃ | H |
| 14. | H | —CH(CH₃)—CH=CH₂ | H |
| 15. | H | —CH₂CH₂CH=CH₂ | H |
| 16. | H | —CH₂CH₂—CH=CH—CH₃ | H |
| 17. | H | —CH(CH₃)—CH₂—CH=CH₂ | H |
| 18. | H | —CH₂—CH(CH₃)—CH=CH₂ | H |
| 19. | H | —CH(CH₃)—C(CH₃)=CH₂ | H |
| 20. | H | —CH(C₂H₅)—CH=CH₂ | H |
| 21. | H | —CH₂—CH=CH—CH₂CH₃ | H |
| 22. | H | —CH₂—CH₂—CH=CH—CH₂CH₃ | H |
| 23. | H | —CH(CH₃)—CH=CH—CH₂CH₃ | H |
| 24. | H | —CH₂—CH(CH₃)—CH=CH₂—CH₃ | H |
| 25. | H | —CH(CH₃)CH₂—CH₂CH₂=CH₂ | H |
| 26. | H |  | H |
| 27. | H |  | H |
| 28. | H |  | H |
| 29. | H |  | H |
| 30. | H | —CH₂— | H |
| 31. | H | —CH₂— | H |
| 32. | H | —CH₂— | H |
| 33. | H | —CH₂— | H |

-continued
| | | | |
|---|---|---|---|
| 34. | H | —CH₂—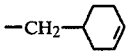 | H |
| 35. | H | —CH₂—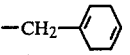 | H |
| 36. | H | —CH₂—CH=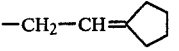 | H |
| 37. | H |  | H |
| 38. | H |  | H |
| 39. | H |  | H |
| 40. | H | —CH₂—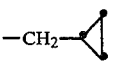 | H |
| 41. | H |  | H |
| 42. | H | —CH₂— | H |
| 43. | H | —CH₂—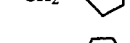 | H |
| 44. | H | —CH₂CH₂—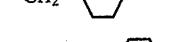 | H |
| 45. | H | 1-adamantyl | |
| 46. | H | —CH₂—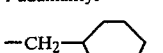 | H |
| 47. | H |  | H |
| 48. | H |  | H |
| 49. | H |  | H |
| 50. | H | 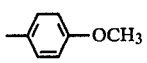 | H |
| 51. | H | 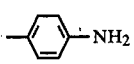 | H |
| 52. | H | —CH₂CH₂N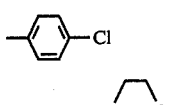 | H |
| 53. | H | —CH₂CH₂—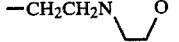 | H |
| 54. | H | —CH—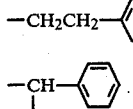\|\nCH₃ | H |
| 55. | H | —CH₂CH=CH— | H |
| 56. | H | —CH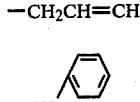 | H |
| 57. | H | —CH₂——OH | H |
| 58. | H | —CH₂——SCH₃ | H |

-continued

| | | | |
|---|---|---|---|
| 59. | H | -CH₂-C₆H₄-N(CH₃)₂ | H |
| 60. | H | -CH₂-C₆H₄-Cl with CH₃ on CH | H |
| 61. | H | —C₂H₅ | —C₂H₅ |
| 62. | H | —CH(CH₃)₂ | —CH(CH₃)₂ |
| 63. | H | —CH₂CH₂CH₃ | —CH₂CH₂CH₃ |
| 64. | H | —CH₃ | —C₂H₅ |
| 65. | H | —CH₃ | —CH(CH₃)₂ |
| 66. | H | —CH₃ | —CH₂CH=CH₂ |
| 67. | H | —CH₂CH=CH₂ | —CH₂CH=CH₂ |
| 68. | H | —C(CH₃)₃ | —CH₃ |
| 69. | H | —CH₃ | —CH(CH₃)—C₂H₅ |
| 70. | H | —C₂H₅ | —CH(CH₃)₂ |
| 71. | H | —CH₃ | —CH(CH₃)CH=CH₂ |
| 72. | H | —CH₃ | —CH₂—CH(CH₃)₂ |
| 73. | H | —CH₃ | —CH₂CH₂CH₃ |
| 74. | H | —CH₃ | —CH₂φ |
| 75. | H | —CH₃ | —φ (phenyl) |
| 76. | H | —CH₃ | —CH₂-(cyclopentenyl) |
| 77. | H | —CH₃ | —CH₂—C(CH₃)=CH₂ |
| 78. | H | —CH₃ | -cyclohexyl |
| 79. | H | —CH₃ | —CH₂-(cyclopropyl) |
| 80. | H | —CH₃ | —CH₂-(thienyl) |
| 81. | —CH₃ | —C₂H₅ | H |
| 82. | —CH₃ | —CH₂CH=CH₂ | H |
| 83. | —CH₃ | —CH(CH₃)₂ | H |
| 84. | —CH=CH₂ | —CH₃ | H |
| 85. | —CH=CH₂ | —C₂H₅ | H |
| 86. | —CH=CH₂ | —CH(CH₃)₂ | H |
| 87. | —CH₃ | —C(CH₃)₃ | H |
| 88. | —CH₃ | —CH₂-(cyclopentenyl) | H |
| 89. | —CH₃ | —CH₂-(cyclopropyl) | H |
| 90. | —CH₃ | -cyclohexyl | H |
| 91. | —CH₃ | —CH₂φ | H |
| 92. | —CH₃ | —CH₂-(pyridyl) | H |
| 93. | —CH₃ | —CH(CH₃)CH=CH₂ | H |
| 94. | —CH₃ | —CH₂—C(CH₃)=CH₂ | H |
| 95. | —CH₃ | —CH(CH₃)—CH₂CH₃ | H |
| 96. | —CH=CH₂ | H | H |
| 97. | —CH₃ | —CH₂-(cyclohexadienyl) | H |
| 98. | —CH₃ | —φ | H |
| 99. | —CH₃ | -(thienyl) | H |

-continued
| | | | |
|---|---|---|---|
| 100. | —CH₃ | 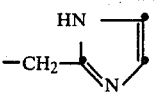 | H |
| 101. | CH₃ | CH₃ | CH₃ |
| 102. | CH₃ | CH₃ | C₂H₅ |
| 103. | CH₃ | CH₃ | —CH(CH₃)₂ |
| 104. | CH₃ | CH₃ | CH₂CH=CH₂ |
| 105. | CH₃ | C₂H₅ | C₂H₅ |
| 106. | CH₃ | CH₃ |  |
| 107. | CH₃ | CH₃ |  |
| 108. | CH₃ | —CH₂CH=CH₃ |  |
| 109. | CH₃ | C₂H₅ |  |
| 110. | CH₃ | CH₃ |  |
| 111. | COOH | H | H |
| 112. | H |  | H |
| 113. | H |  | H |
| 114. | H |  | H |
| 115. | H | 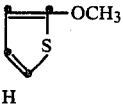 | H |
| 116. |  | H | H |
| 117. | H |  | H |
| 118. |  | H | H |
| 119. | H | 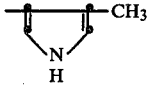 | H |
| 120. | H | 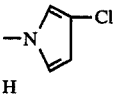 | H |
| 121. |  | H | H |
| 122. | H | 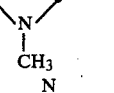 | H |
| 123. | 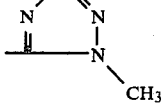 | H | H |
| 124. |  | H | H |

-continued
| | | | |
|---|---|---|---|
| 125. | H | 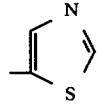 | H |
| 126. | H | 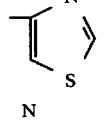 | H |
| 127. | H | 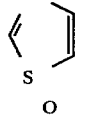 | H |
| 128. | H | 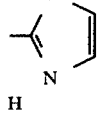 | H |
| 129. | 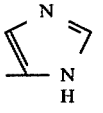 | H | H |
| 130. | H | 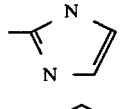 | H |
| 131. | H | 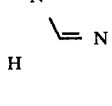 | H |
| 132. | 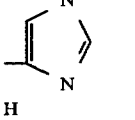 | H | H |
| 133 | H | 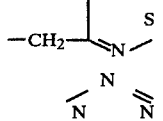 | H |
| 134. | H | 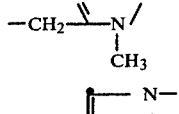 | H |
| 135. | H | 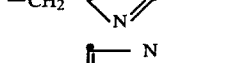 | H |
| 136. | H | 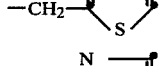 | H |
| 137. | H | 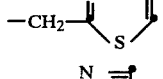 | H |
| 138. | H | 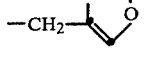 | H |
| 139. | H | 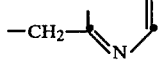 | H |
| 140. | H | 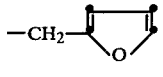 | H |
| 141. | H | 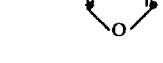 | H |

-continued

| # | R1 | R2 | R3 |
|---|----|----|----|
| 142. | H | —CH₂-(thiophene) | H |
| 143. | H | —CH₂-(thiophene) | H |
| 144. | H | —CH₂-(4-pyridyl) | H |
| 145. | H | —CH₂-(3-pyridyl) | H |
| 146. | H | —CH₂-(2-dihydropyridyl) | H |
| 147. | H | —CH₂-(dihydropyrimidinyl) | H |
| 148. | H | —CH₂—CH₂-(2-pyridyl) | H |
| 149. | H | —CH₂-(benzimidazolyl) | H |
| 150. | φ—CH₂ | H | H |
| 151. | (4-pyridyl)—CH₂— | H | H |
| 152. | H | —CH₂—O—CH₃ | H |
| 153. | H | —CH₂CH₂—O—CH₃ | H |
| 154. | CH₃ | —CH₂CH₂—S—CH₃ | H |
| 155. | H | —CH₂CH₂—OH | H |
| 156. | H | —CH₂CH(OCH₃)—CH₃ | H |
| 157. | H | —CH₂CH₂—CH₂—C≡N | H |
| 158. | H | —CH₂CH₂CH—(OCH₃)₂ | H |
| 159. | H | —CH₂—C(O)—φ | H |
| 160. | H | —CH(CH₂OH)—CH₂CH₃ | H |
| 161. | H | —CH₂CH₂CONH₂ | H |
| 162. | H | —CH₂COOC₂H₅ | H |
| 163. | H | —C(CH₃)CH₂CH₂CH₂N(C₂H₅)₂ | H |
| 164. | H | —CH₂CH₂—SH | H |
| 165. | H | —CH(CH₃)—(4-hydroxyphenyl) | H |
| 166. | H | —CH₂CH₂—N(CH₃)₂ | H |
| 167. | H | —CH₂CH₂CH₂—Br | H |
| 168. | H | —CH₂CH₂CH—N(CH₃)₂ | H |
| 169. | H | —CH₂CH₂—N(CH₃)₃ | H |
| 170. | NH₂ | CH₃ | H |
| 171. | NH₂ | CH₃ | CH₃ |
| 172. | NHCH₃ | CH₃ | CH₃ |
| 173. | N(CH₃)₂ | CH₃ | CH₃ |
| 174. | NH₂ | C₂H₅ | H |
| 175. | NH₂ | —CH(CH₃)₂ | H |
| 176. | NH₂ | —CHCH=CH₂ | H |
| 177. | NHCH₃ | —CH(CH₃)₂ | H |

-continued

| | | | |
|---|---|---|---|
| 178. | NHCH$_3$ | CH$_3$ | H |
| 179. | NH$_2$ | N(CH$_3$)$_2$ | H |
| 180. | NH$_2$ | NHNH$_2$ | H |
| 181. | OCH$_3$ | H | H |
| 182. | OCH$_3$ | CH$_3$ | H |
| 183. | OCH$_3$ | CH$_3$ | CH$_3$ |
| 184. | OCH$_3$ | C$_2$H$_5$ | H |
| 185. | OCH$_3$ | CH(CH$_3$)$_2$ | H |
| 186. | OCH$_3$ | H | H |
| 187. | SCH$_3$ | CH$_3$ | H |
| 188. | SCH$_3$ | CH$_3$ | CH$_3$ |
| 189. | SCH$_3$ | CH(CH$_3$)$_2$ | H |
| 190. | S—CH$_2$—CH=CH$_2$ | CH$_3$ | H |
| 191. | S—CH$_2$—φ | CH$_3$ | H |
| 192. | —SCH$_2$CH=CH$_2$ | H | H |
| 193. | SCH$_2$φ | H | H |
| 194. | H | —OH | H |
| 195. | H | —OCH$_3$ | H |
| 196. | CH$_3$ | —OH | H |
| 197. | H | —C≡N | H |
| 198. | H | —NHCH$_3$ | H |
| 199. | H | NH$_2$ | H |
| 200. | CH$_3$ | CH$_3$ | NH$_2$ |
| 201. | H | CH$_3$ | N(CH$_3$)$_2$ |
| 202. | CH$_2$Br | H | H |
| 203. | —CH$_2$N(CH$_3$)$_2$ | H | H |
| 204. | —CH$_2$S—CH$_3$ | H | H |
| 205. | $-\overset{O}{\overset{\|}{C}}-NH_2$ | H | H |
| 206. | —CH$_2$N(CH$_3$)$_3$ | H | H |
| 207. | —C(CH$_3$)$_3$ | H | —C(CH$_3$)$_3$ |
| 208. | —CHCH$_3$<br>\|<br>CH$_3$ | CH$_3$ | —CHCH$_3$<br>\|<br>CH$_3$ |
| 209. | —CHCH$_3$<br>\|<br>CH$_3$ | —CHCH$_3$<br>\|<br>CH$_3$ | —CHCH$_3$<br>\|<br>CH$_3$ |
| 210. | —C(CH$_3$)$_3$ | —C(CH$_3$)$_3$ | —C(CH$_3$)$_3$ |

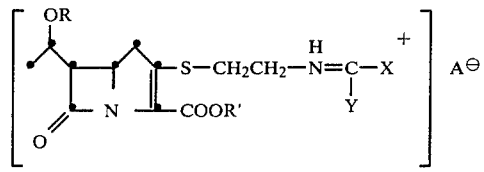

| Compound | R | R' | X | Y | A |
|---|---|---|---|---|---|
| 211. | H | —CH$_2$CH=C(CH$_3$)$_2$ | NH$_2$ | H | Cl |
| 212. | H | —CH$_2$—⌬—OCH$_3$ | NH$_2$ | H | Cl |
| 213. | H | —CH$_2$—O—C(=O)—C(CH$_3$)$_3$ | NHCH$_3$ | H | HSO$_4$ |
| 214. | H | —CH$_2$—O—C(=O)—C(CH$_3$)$_3$ | NH$_2$ | CH$_3$ | CH$_3$COO |
| 215. | H | —CH$_2$CH$_2$—CH=CH$_2$ | NHCH(CH$_3$)$_2$ | H | Cl |
| 216. | H | —CH$_2$CH$_2$—S—CH$_3$ | NHCH$_3$ | CH$_3$ | H$_2$PO$_4$ |
| 217. | H | —CH$_2$—O—C(=O)—CH$_3$ | NHCH$_3$ | CH$_3$ | Cl |
| 218. | H | —CH$_2$—C(=O)—φ | NH$_2$ | H | Cl |
| 219. | H | -5 indanyl | N(CH$_3$)$_2$ | H | Cl |
| 220. | H | -phthalidyl | —CH$_2$CH=CH$_2$ | H | Cl |
| 221. | SO$_3^-$ | Na | NH$_2$ | H | — |
| 222. | PO$_4$H$_2$ | —CH$_2$OCC(CH$_3$)<br>‖<br>O | NH$_2$ | CH$_3$ | — |
| 223. | SO$_3^-$ | —CH$_2$—CH=C(CH$_3$)$_2$ | NHCH$_3$ | H | — |
| 224. | PO$_4$H$_2$ | Na | NHCH(CH$_3$)$_2$ | H | — |

EXAMPLE 54

Preparation of Pharmaceutical Compositions

One such unit dosage form consists in mixing 120 mg. of N-acetimidoyl Thienamycin (product of Example 12) with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
| --- | --- |
| N-acetimidoyl Thienamycin | 125 mg. |
| Cornsatarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| Ampoule: | |
| --- | --- |
| PARENTERAL SOLUTION | |
| N-acetimidoyl Thienamycin | 500 mg. |
| Sterile water | 2 ml. |
| OPTHALMIC SOLUTION | |
| N-acetimidoyl Thienamycin | 100 mg. |
| Hydroxypropylmethyl cellulose | 5 mg. |
| Sterile Water | to 1 ml. |
| OTIC SOLUTION | |
| N-acetimidoyl Thienamycin | 100 mg. |
| Benzalkonium Chloride | 0.1 mg. |
| Sterile Water | to 1 ml. |
| TOPICAL OINTMENT | |
| N-acetimidoyl | |

| Ampoule: | |
| --- | --- |
| Thienamycin | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. The compound having the following structure

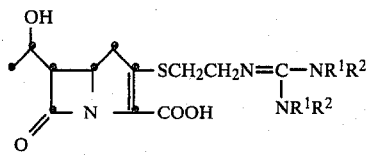

wherein $R^1$ and $R^2$ are independently selected from the group consisting of: hydrogen, substituted and unsubstituted: alkyl having 1–6 carbon atoms; alkenyl having 3–6 carbon atoms; cycloalkyl, cycloalkylalkyl, cycloalkenyl, and cycloalkenylalkyl having 3–6, 4–7, 4–6 and 4–7 carbon atoms, respectively; nitro; amino; mono- or di-alkylamino, wherein the alkyl moieties each comprises 1–6 carbon atoms; or benzyl, thienylalkyl, furylalkyl or pyridylalkyl, wherein alkyl is 1–3 carbon atoms; wherein the ring or chain substituent or substituents relative to the definition of $R^1$ and $R^2$ are mono-substituents or disubstituents selected from the group consisting of chloro, fluoro, hydroxyl, alkoxyl having 1–3 carbon atoms, dialkylamino having 1–3 carbon atoms in each alkyl moiety, and alkylthio having 1–3 carbon atoms.

2. The compound according to claim 1 wherein: $R^1$ and $R^2$ are independently selected from the group consisting of: hydrogen; alkyl; alkenyl; nitro; and amino.

3. The compound having the following structure

[structure diagram showing compound with OH, SCH$_2$CH$_2$N=C(NH$_2$)(NH$_2$), COOH, and β-lactam ring]

* * * * *